(12) United States Patent
Mody et al.

(10) Patent No.: US 11,342,081 B2
(45) Date of Patent: May 24, 2022

(54) PRIVACY-ENHANCED CONTACT TRACING USING MOBILE APPLICATIONS AND PORTABLE DEVICES

(71) Applicant: ServiceNow, Inc., Santa Clara, CA (US)

(72) Inventors: Yamit Mody, San Diego, CA (US); Sheehan Alam, San Diego, CA (US); Adam Golab, Santa Clara, CA (US); Yevgeniy Goldin, San Francisco, CA (US); Senthil Rajavallipuram Meenakshisundaram, Santa Clara, CA (US); Anita Ranganath, Santa Clara, CA (US); Adam Danial Yanalunas, San Diego, CA (US); Probir Das, Santa Clara, CA (US)

(73) Assignee: ServiceNow, Inc., Santa Clara, CA (US)

( * ) Notice: Subject to any disclaimer, the term of this patent is extended or adjusted under 35 U.S.C. 154(b) by 93 days.

(21) Appl. No.: 17/076,218

(22) Filed: Oct. 21, 2020

(65) Prior Publication Data

US 2022/0122741 A1 Apr. 21, 2022

(51) Int. Cl.
*G16H 50/80* (2018.01)
*G16H 10/60* (2018.01)
(Continued)

(52) U.S. Cl.
CPC .......... *G16H 50/80* (2018.01); *G06Q 50/265* (2013.01); *G16H 10/60* (2018.01); *G16H 70/60* (2018.01);
(Continued)

(58) Field of Classification Search
CPC ..... G16H 50/80; G16H 70/60; H04W 12/088; H04W 4/023; H04W 4/20; G06Q 50/265
See application file for complete search history.

(56) References Cited

U.S. PATENT DOCUMENTS

| 4,941,084 A | 7/1990 | Terada et al. |
| 5,185,860 A | 2/1993 | Wu |

(Continued)

FOREIGN PATENT DOCUMENTS

| EP | 0433979 | 6/1991 |
| EP | 1607824 | 12/2005 |

(Continued)

OTHER PUBLICATIONS

"ServiceNow Contact Tracing", servicenow, Data Sheet, 2020.
"Paris HR Service Delivery" servicenow, Aug. 20, 2020.

*Primary Examiner* — Curtis B Odom
(74) *Attorney, Agent, or Firm* — McDonnell Boehnen Hulbert & Berghoff LLP

(57) ABSTRACT

A embodiment may involve receiving a contact tracing request for a first user identifier that corresponds to a first portable device identifier of a first portable device. The second example embodiment may also involve requesting and receiving, from a first computing device associated with the first user identifier, device adjacency data, wherein the device adjacency data contains a plurality of contact entries, wherein one of the contact entries identifies a second portable device identifier of a second portable device that was wirelessly detected by the first portable device and a timestamp of when the wireless detection of the second portable device occurred. The second example embodiment may involve determining, from the mappings, a second user identifier that corresponds to the second portable device identifier. The second example embodiment may further involve transmitting, to a second computing device associated with the second user identifier, a contact tracing notification.

20 Claims, 13 Drawing Sheets

(51) Int. Cl.
*G16H 70/60* (2018.01)
*H04W 4/02* (2018.01)
*H04W 4/20* (2018.01)
*G06Q 50/26* (2012.01)
*H04W 12/088* (2021.01)
*H04W 4/80* (2018.01)

(52) U.S. Cl.
CPC ............ *H04W 4/023* (2013.01); *H04W 4/20* (2013.01); *H04W 12/088* (2021.01); *H04W 4/80* (2018.02)

(56) References Cited

U.S. PATENT DOCUMENTS

| | | | |
|---|---|---|---|
| 5,237,518 A | 8/1993 | Sztipanovits et al. | |
| 5,261,097 A | 11/1993 | Saxon | |
| 5,265,252 A | 11/1993 | Rawson, III et al. | |
| 5,367,685 A | 11/1994 | Gosling | |
| 5,390,297 A | 2/1995 | Barber et al. | |
| 5,442,791 A | 8/1995 | Wrabetz et al. | |
| 5,452,415 A | 9/1995 | Hotka | |
| 5,522,042 A | 5/1996 | Fee et al. | |
| 5,533,116 A | 7/1996 | Vesterinen | |
| 5,655,081 A | 8/1997 | Bonnell et al. | |
| 5,659,736 A | 8/1997 | Hasegawa et al. | |
| 5,671,412 A | 9/1997 | Christiano | |
| 5,696,701 A | 12/1997 | Burgess et al. | |
| 5,715,463 A | 2/1998 | Merkin | |
| 5,745,879 A | 4/1998 | Wyman | |
| 5,761,502 A | 6/1998 | Jacobs | |
| 5,764,913 A | 6/1998 | Jancke et al. | |
| 5,887,139 A | 3/1999 | Madison, Jr. et al. | |
| 5,909,217 A | 6/1999 | Bereiter | |
| 5,937,165 A | 8/1999 | Schwaller et al. | |
| 5,949,976 A | 9/1999 | Chappelle | |
| 5,978,594 A | 11/1999 | Bonnell et al. | |
| 6,021,437 A | 2/2000 | Chen et al. | |
| 6,041,347 A | 3/2000 | Harsham et al. | |
| 6,088,717 A | 7/2000 | Reed et al. | |
| 6,101,500 A | 8/2000 | Lau | |
| 6,128,016 A | 10/2000 | Coelho et al. | |
| 6,131,118 A | 10/2000 | Stupek, Jr. et al. | |
| 6,134,581 A | 10/2000 | Ismael et al. | |
| 6,138,122 A | 10/2000 | Smith et al. | |
| 6,148,335 A | 11/2000 | Haggard et al. | |
| 6,166,732 A | 12/2000 | Mitchell et al. | |
| 6,167,448 A | 12/2000 | Hemphill et al. | |
| 6,175,866 B1 | 1/2001 | Holloway et al. | |
| 6,175,878 B1 | 1/2001 | Seaman et al. | |
| 6,260,050 B1 | 7/2001 | Yost et al. | |
| 6,263,457 B1 | 7/2001 | Anderson et al. | |
| 6,272,150 B1 | 8/2001 | Hrastar et al. | |
| 6,336,138 B1 | 1/2002 | Caswell et al. | |
| 6,363,421 B2 | 3/2002 | Barker et al. | |
| 6,393,386 B1 | 5/2002 | Zager et al. | |
| 6,397,245 B1 | 5/2002 | Johnson, II et al. | |
| 6,434,626 B1 | 8/2002 | Prakash et al. | |
| 6,438,592 B1 | 8/2002 | Killian | |
| 6,456,306 B1 | 9/2002 | Chin et al. | |
| 6,466,932 B1 | 10/2002 | Dennis et al. | |
| 6,487,590 B1 | 11/2002 | Foley et al. | |
| 6,505,248 B1 | 1/2003 | Casper et al. | |
| 6,526,442 B1 | 2/2003 | Stupek, Jr. et al. | |
| 6,621,823 B1 | 9/2003 | Mellquist et al. | |
| 6,707,795 B1 | 3/2004 | Noorhosseini et al. | |
| 6,742,015 B1 | 5/2004 | Bowman-Amuah | |
| 6,763,380 B1 | 7/2004 | Mayton et al. | |
| 6,816,898 B1 | 11/2004 | Scarpelli et al. | |
| 6,895,586 B1 | 5/2005 | Brasher et al. | |
| 6,948,175 B1 | 9/2005 | Fong et al. | |
| 6,985,901 B1 | 1/2006 | Sachse et al. | |
| 7,003,564 B2 | 2/2006 | Greuel et al. | |
| 7,028,228 B1 | 4/2006 | Lovy et al. | |
| 7,043,537 B1 | 5/2006 | Pratt | |
| 7,043,661 B2 | 5/2006 | Valadarsky et al. | |
| 7,062,683 B2 | 6/2006 | Warpenburg et al. | |
| 7,096,459 B2 | 8/2006 | Keller et al. | |
| 7,146,574 B2 | 12/2006 | Goldthwaite et al. | |
| 7,197,466 B1 | 3/2007 | Peterson et al. | |
| 7,215,360 B2 | 5/2007 | Gupta | |
| 7,216,304 B1 | 5/2007 | Gourdol et al. | |
| 7,222,147 B1 | 5/2007 | Black et al. | |
| 7,281,170 B2 | 10/2007 | Taylor et al. | |
| 7,412,502 B2 | 8/2008 | Fearn et al. | |
| 7,505,872 B2 | 3/2009 | Keller et al. | |
| 7,593,013 B2 | 9/2009 | Agutter et al. | |
| 7,596,716 B2 | 9/2009 | Frost et al. | |
| 7,617,073 B2 | 11/2009 | Trinon et al. | |
| 7,660,731 B2 | 2/2010 | Chaddha et al. | |
| 7,676,294 B2 | 3/2010 | Baier et al. | |
| 7,676,437 B2 | 3/2010 | Satkunanathan et al. | |
| 7,840,490 B1 | 11/2010 | Sellers et al. | |
| 7,877,783 B1 | 1/2011 | Cline et al. | |
| 7,890,869 B1 | 2/2011 | Mayer et al. | |
| 7,966,398 B2 | 6/2011 | Wiles, Jr. | |
| 8,060,396 B1 | 11/2011 | Bessler et al. | |
| 8,196,210 B2 | 6/2012 | Sterin | |
| 8,321,948 B2 | 11/2012 | Robinson et al. | |
| 8,407,669 B2 | 3/2013 | Yee et al. | |
| 8,554,750 B2 | 10/2013 | Rangarajan et al. | |
| 8,595,647 B2 | 11/2013 | Sabin et al. | |
| 8,620,818 B2 | 12/2013 | Hughes et al. | |
| 8,646,093 B2 | 2/2014 | Myers et al. | |
| 8,674,992 B2 | 3/2014 | Poston et al. | |
| 8,725,647 B2 | 5/2014 | Disciascio et al. | |
| 9,053,460 B2 | 6/2015 | Gilbert et al. | |
| 9,098,555 B2 | 8/2015 | Bjork et al. | |
| 10,079,730 B2 | 9/2018 | Subramanian et al. | |
| 2002/0116340 A1 | 8/2002 | Hellberg et al. | |
| 2002/0133584 A1 | 9/2002 | Greuel et al. | |
| 2002/0158969 A1 | 10/2002 | Gupta | |
| 2003/0118087 A1 | 6/2003 | Goldthwaite et al. | |
| 2003/0200293 A1 | 10/2003 | Fearn et al. | |
| 2005/0015217 A1 | 1/2005 | Weidl et al. | |
| 2005/0091356 A1 | 4/2005 | Izzo | |
| 2006/0026453 A1 | 2/2006 | Frost et al. | |
| 2006/0095461 A1 | 5/2006 | Raymond | |
| 2006/0179058 A1 | 8/2006 | Bram et al. | |
| 2006/0293942 A1 | 12/2006 | Chaddha et al. | |
| 2007/0033279 A1 | 2/2007 | Battat et al. | |
| 2007/0188494 A1 | 8/2007 | Agutter et al. | |
| 2007/0288389 A1 | 12/2007 | Vaughan et al. | |
| 2008/0133289 A1 | 6/2008 | Armour et al. | |
| 2008/0148253 A1 | 6/2008 | Badwe et al. | |
| 2008/0319779 A1 | 12/2008 | Hughes et al. | |
| 2009/0088875 A1 | 4/2009 | Baier et al. | |
| 2009/0228984 A1 | 9/2009 | Sterin | |
| 2010/0110932 A1 | 5/2010 | Doran et al. | |
| 2012/0016706 A1 | 1/2012 | Pargaonkar et al. | |
| 2021/0365445 A1* | 11/2021 | Robell | H04L 63/00 |

FOREIGN PATENT DOCUMENTS

| | | |
|---|---|---|
| WO | WO 99/34285 | 7/1999 |
| WO | WO 00/52559 | 9/2000 |
| WO | WO 01/79970 | 10/2001 |

* cited by examiner

PRIVACY-ENHANCED CONTACT TRACING USING MOBILE APPLICATIONS AND PORTABLE DEVICES

BACKGROUND

Infectious diseases may be easily transmitted from one human to another, affecting significant portions of a population in one or more regions. The highly contagious nature and potentially serious effects of infectious diseases to personal and public health may drive the implementation of various preventative measures. These measures, while necessary to limit spread, can be extremely costly to the economy and society at large.

For instance, the COVID-19 pandemic was caused by severe acute respiratory syndrome coronavirus 2 (SARS-CoV-2). The World Health Organization (WHO) reported that, around six months after the first case was confirmed, over 12 million people globally were infected. The COVID-19 pandemic caused governments and businesses to implement prevention measures to reduce the spread of illness, including strategies broadly centered on restricting person-to-person spread in populations. Due to COVID-19 and the related prevention measures, the World Bank projected a contraction of 5.2 percent in global gross domestic product in 2020. For primarily similar reasons, the World Bank further projected ongoing losses caused by the decreased quality of schooling, instruction lost from school closures, etc.

In an effort to lower economic and societal cost of long term restrictions on movement and gatherings, more specific measures were implemented to target individuals, including testing symptomatic individuals, contact tracing of individuals with whom the symptomatic individuals were in close proximity, and subsequently restricting contact with the symptomatic individuals and those who were exposed to symptomatic individuals. These measures were met with mixed success. Tracing contacts between individuals has proved to be time consuming and logistically difficult in the population at large of some countries and regions. Technological solutions, such as using mobile devices to track locations of individuals, were also employed. However, these efforts provoked a range of concerns relating to personal privacy, such as governmental and/or corporate access to location and contact data. Consequently, implementing contact tracing on a wide scale while respecting certain privacy rights of individuals has had little success.

SUMMARY

In order to overcome these and possibly other challenges, contact tracing functionality and data storage relating to user and/or user device interactions may be spread over multiple devices such that a user may have a level of control over the data collected. For example, the embodiments herein may use portable devices capable of communicating by way of personal area networks (e.g., BLUETOOTH® Low Energy devices, otherwise referred to as BLE devices) to collect semi-anonymous data on users who may have had contact with one another. These embodiments may also use mobile devices to store the collected data, and a server-based computational instance to store mappings between portable device identifiers and identifiers of users.

Within an enterprise, users who are on premise may each be issued a portable device. These devices may be worn or carried by the users and are capable of short-distance wireless communication (e.g., over several meters). The portable devices may be associated (e.g., paired) with the mobile devices of their respective users, and therefore capable of communicating wirelessly with their associated mobile devices.

The portable devices may be used to detect the presence of, and exchange information with, other portable devices worn or carried by other users in wireless range. When a first portable device detects a second portable device, these devices may exchange their respective portable device identifiers. Each of the portable devices records the portable device identifier of the other portable device, and provides a record of the transaction, along with a timestamp of when the transaction took place, to their respective mobile devices.

The mobile devices may be computing devices capable of communicating wirelessly with their associated portable devices, as well as by way of the Internet (e.g., through a Wifi or cellular data connection). As examples, the mobile devices could be cellular phones, tablets, or laptop computers. Device adjacency data stored in each mobile device may contain the contact entries (portable device identifiers and timestamps) received from the associated portable devices. These data may contain little or no further information. In particular, names or other information that could be used to directly and easily identify users may be omitted. This prevents a user of one of the mobile devices from being able to easily identify other individuals with whom he or she had contact from the stored device adjacency data.

Nonetheless, the computational instance introduced above may include one or more remote server devices that do contain mappings between portable device identifiers, identifiers of users (e.g., names or employee numbers) to whom the associated portable devices were issued, as well as mobile device identifiers of these users. These mappings may be stored in a database disposed within the computational instance. The database table and/or entries therein containing the mappings may be encrypted so that access is restricted to a person or persons with the decryption key. This prevents most users and administrators of the computational instance from being able to view the mappings.

When a particular user reports that he or she is subject to an adverse condition (e.g., is symptomatic, has tested positive for a pathogen, or may have been exposed to a pathogen), this information may be entered into the computational instance. In response, the computational instance may request and receive the device adjacency data from the mobile device of the particular user. From the contact entries therein, the computational instance may generate a list of portable device identifiers of portable devices that the particular user was in proximity to over a particular window of time (e.g., the previous two weeks). With this information, the computational instance may use the mappings to notify each user associated with a portable device referenced by the list. Further, the computational instance may recursively gather device adjacency data from the notified users, identify when these users were in proximity to additional users, and expand the contact tracing (e.g., to second-order and/or third-order contacts of the particular user).

The distributed system of contact tracing and data storage as described above limits access to device adjacency data and mappings so that no one user has access to more information than is needed at any point in time to carry out contact tracing. This system may also allow users to exert a level of control over the data collected. For example, if contact tracing was done in an enterprise so that employees may work and interact with coworkers in a safe manner, the employee may disconnect the portable device from their mobile device when not at work. Thus, privacy concerns may be addressed while aggressive contact tracing is still possible within an organizational setting.

Accordingly, a first example embodiment may involve persistent storage containing mappings between user identifiers and portable device identifiers respectively corresponding to the user identifiers. The first example embodiment may further involve one or more processors configured to: receive a contact tracing request for a first user identifier that corresponds in the mappings to a first portable device identifier of a first portable device; request and receive, from a first computing device associated with the first user identifier, device adjacency data, wherein the device adjacency data contains a plurality of contact entries, wherein one of the contact entries identifies: (i) a second portable device identifier of a second portable device that was wirelessly detected by the first portable device, and (ii) a timestamp of when the wireless detection of the second portable device occurred; determine, from the mappings, a second user identifier that corresponds to the second portable device identifier; and transmit, to a second computing device associated with the second user identifier, a contact tracing notification.

A second example embodiment may involve receiving a contact tracing request for a first user identifier that corresponds to a first portable device identifier of a first portable device, wherein persistent storage contains mappings between user identifiers and portable device identifiers respectively corresponding to the user identifiers. The second example embodiment may also involve requesting and receiving, from a first computing device associated with the first user identifier, device adjacency data, wherein the device adjacency data contains a plurality of contact entries, wherein one of the contact entries identifies: (i) a second portable device identifier of a second portable device that was wirelessly detected by the first portable device, and (ii) a timestamp of when the wireless detection of the second portable device occurred. The second example embodiment may also involve determining, from the mappings, a second user identifier that corresponds to the second portable device identifier. The second example embodiment may further involve transmitting, to a second computing device associated with the second user identifier, a contact tracing notification.

In a third example embodiment, an article of manufacture may include a non-transitory computer-readable medium, having stored thereon program instructions that, upon execution by a computing system, cause the computing system to perform operations in accordance with the first and/or second example embodiment.

In a fourth example embodiment, a system may include various means for carrying out each of the operations of the first and/or second example embodiment.

These, as well as other embodiments, aspects, advantages, and alternatives, will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Figure 1:
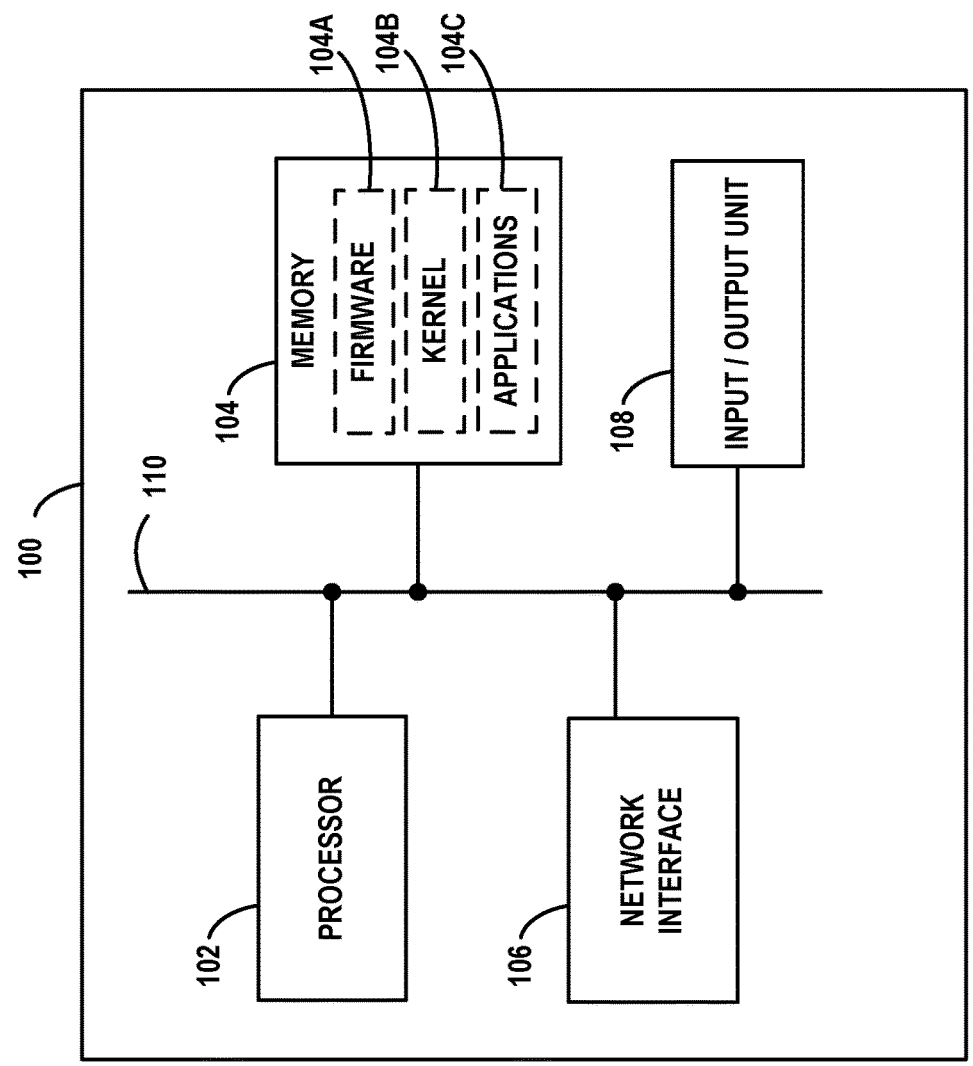
FIG. 1 illustrates a schematic drawing of a computing device, in accordance with example embodiments.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features unless stated as such. Thus, other embodiments can be utilized and other changes can be made without departing from the scope of the subject matter presented herein. Accordingly, the example embodiments described herein are not meant to be limiting. It will be readily understood that the aspects of the present disclosure, as generally described herein, and illustrated in the figures, can be arranged, substituted, combined, separated, and designed in a wide variety of different configurations. For example, the separation of features into "client" and "server" components may occur in a number of ways.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

I. Introduction

A large enterprise is a complex entity with many interrelated operations. Some of these are found across the enterprise, such as human resources (HR), supply chain, information technology (IT), and finance. However, each enterprise also has its own unique operations that provide essential capabilities and/or create competitive advantages.

To support widely-implemented operations, enterprises typically use off-the-shelf software applications, such as customer relationship management (CRM) and human capital management (HCM) packages. However, they may also need custom software applications to meet their own unique requirements. A large enterprise often has dozens or hundreds of these custom software applications. Nonetheless, the advantages provided by the embodiments herein are not limited to large enterprises and may be applicable to an enterprise, or any other type of organization, of any size.

Many such software applications are developed by individual departments within the enterprise. These range from simple spreadsheets to custom-built software tools and databases. But the proliferation of siloed custom software applications has numerous disadvantages. It negatively impacts an enterprise's ability to run and grow its operations, innovate, and meet regulatory requirements. The enterprise may find it difficult to integrate, streamline, and enhance its operations due to lack of a single system that unifies its subsystems and data.

To efficiently create custom applications, enterprises would benefit from a remotely-hosted application platform that eliminates unnecessary development complexity. The goal of such a platform would be to reduce time-consuming, repetitive application development tasks so that software engineers and individuals in other roles can focus on developing unique, high-value features.

In order to achieve this goal, the concept of Application Platform as a Service (aPaaS) is introduced, to intelligently automate workflows throughout the enterprise. An aPaaS system is hosted remotely from the enterprise, but may access data, applications, and services within the enterprise by way of secure connections. Such an aPaaS system may have a number of advantageous capabilities and characteristics. These advantages and characteristics may be able to improve the enterprise's operations and workflows for IT, HR, CRM, customer service, application development, and security.

The aPaaS system may support development and execution of model-view-controller (MVC) applications. MVC applications divide their functionality into three interconnected parts (model, view, and controller) in order to isolate representations of information from the manner in which the information is presented to the user, thereby allowing for efficient code reuse and parallel development. These applications may be web-based, and offer create, read, update, delete (CRUD) capabilities. This allows new applications to be built on a common application infrastructure.

The aPaaS system may support standardized application components, such as a standardized set of widgets for graphical user interface (GUI) development. In this way, applications built using the aPaaS system have a common look and feel. Other software components and modules may be standardized as well. In some cases, this look and feel can be branded or skinned with an enterprise's custom logos and/or color schemes.

The aPaaS system may support the ability to configure the behavior of applications using metadata. This allows application behaviors to be rapidly adapted to meet specific needs. Such an approach reduces development time and increases flexibility. Further, the aPaaS system may support GUI tools that facilitate metadata creation and management, thus reducing errors in the metadata.

The aPaaS system may support clearly-defined interfaces between applications, so that software developers can avoid unwanted inter-application dependencies. Thus, the aPaaS system may implement a service layer in which persistent state information and other data are stored.

The aPaaS system may support a rich set of integration features so that the applications thereon can interact with legacy applications and third-party applications. For instance, the aPaaS system may support a custom employee-onboarding system that integrates with legacy HR, IT, and accounting systems.

The aPaaS system may support enterprise-grade security. Furthermore, since the aPaaS system may be remotely hosted, it should also utilize security procedures when it interacts with systems in the enterprise or third-party networks and services hosted outside of the enterprise. For example, the aPaaS system may be configured to share data amongst the enterprise and other parties to detect and identify common security threats.

Other features, functionality, and advantages of an aPaaS system may exist. This description is for purpose of example and is not intended to be limiting.

As an example of the aPaaS development process, a software developer may be tasked to create a new application using the aPaaS system. First, the developer may define the data model, which specifies the types of data that the application uses and the relationships therebetween. Then, via a GUI of the aPaaS system, the developer enters (e.g., uploads) the data model. The aPaaS system automatically creates all of the corresponding database tables, fields, and relationships, which can then be accessed via an object-oriented services layer.

In addition, the aPaaS system can also build a fully-functional MVC application with client-side interfaces and server-side CRUD logic. This generated application may serve as the basis of further development for the user. Advantageously, the developer does not have to spend a large amount of time on basic application functionality. Further, since the application may be web-based, it can be accessed from any Internet-enabled client device. Alternatively or additionally, a local copy of the application may be able to be accessed, for instance, when Internet service is not available.

The aPaaS system may also support a rich set of pre-defined functionality that can be added to applications. These features include support for searching, email, templating, workflow design, reporting, analytics, social media, scripting, mobile-friendly output, and customized GUIs.

Such an aPaaS system may represent a GUI in various ways. For example, a server device of the aPaaS system may generate a representation of a GUI using a combination of HTML and JAVASCRIPT®. The JAVASCRIPT® may include client-side executable code, server-side executable code, or both. The server device may transmit or otherwise provide this representation to a client device for the client device to display on a screen according to its locally-defined look and feel. Alternatively, a representation of a GUI may take other forms, such as an intermediate form (e.g., JAVA® byte-code) that a client device can use to directly generate graphical output therefrom. Other possibilities exist.

Further, user interaction with GUI elements, such as buttons, menus, tabs, sliders, checkboxes, toggles, etc. may be referred to as "selection", "activation", or "actuation" thereof. These terms may be used regardless of whether the GUI elements are interacted with by way of keyboard, pointing device, touchscreen, or another mechanism.

An aPaaS architecture is particularly powerful when integrated with an enterprise's network and used to manage such a network. The following embodiments describe architectural and functional aspects of example aPaaS systems, as well as the features and advantages thereof.

II. Example Computing Devices and Cloud-Based Computing Environments

FIG. 1 is a simplified block diagram exemplifying a computing device 100, illustrating some of the components that could be included in a computing device arranged to operate in accordance with the embodiments herein. Computing device 100 could be a client device (e.g., a device actively operated by a user), a server device (e.g., a device that provides computational services to client devices), or some other type of computational platform. Some server devices may operate as client devices from time to time in order to perform particular operations, and some client devices may incorporate server features.

In this example, computing device 100 includes processor 102, memory 104, network interface 106, and input/output unit 108, all of which may be coupled by system bus 110 or a similar mechanism. In some embodiments, computing device 100 may include other components and/or peripheral devices (e.g., detachable storage, printers, and so on).

Processor 102 may be one or more of any type of computer processing element, such as a central processing unit (CPU), a co-processor (e.g., a mathematics, graphics, or encryption co-processor), a digital signal processor (DSP), a network processor, and/or a form of integrated circuit or controller that performs processor operations. In some cases, processor 102 may be one or more single-core processors. In other cases, processor 102 may be one or more multi-core processors with multiple independent processing units. Processor 102 may also include register memory for temporarily storing instructions being executed and related data, as well as cache memory for temporarily storing recently-used instructions and data.

Memory 104 may be any form of computer-usable memory, including but not limited to random access memory (RAM), read-only memory (ROM), and non-volatile memory (e.g., flash memory, hard disk drives, solid state drives, compact discs (CDs), digital video discs (DVDs), and/or tape storage). Thus, memory 104 represents both main memory units, as well as long-term storage. Other types of memory may include biological memory.

Memory 104 may store program instructions and/or data on which program instructions may operate. By way of example, memory 104 may store these program instructions on a non-transitory, computer-readable medium, such that the instructions are executable by processor 102 to carry out any of the methods, processes, or operations disclosed in this specification or the accompanying drawings.

As shown in FIG. 1, memory 104 may include firmware 104A, kernel 104B, and/or applications 104C. Firmware 104A may be program code used to boot or otherwise initiate some or all of computing device 100. Kernel 104B may be an operating system, including modules for memory management, scheduling and management of processes, input/output, and communication. Kernel 104B may also include device drivers that allow the operating system to communicate with the hardware modules (e.g., memory units, networking interfaces, ports, and buses) of computing device 100. Applications 104C may be one or more userspace software programs, such as web browsers or email clients, as well as any software libraries used by these programs. Memory 104 may also store data used by these and other programs and applications.

Network interface 106 may take the form of one or more wireline interfaces, such as Ethernet (e.g., Fast Ethernet, Gigabit Ethernet, and so on). Network interface 106 may also support communication over one or more non-Ethernet media, such as coaxial cables or power lines, or over wide-area media, such as Synchronous Optical Networking (SONET) or digital subscriber line (DSL) technologies. Network interface 106 may additionally take the form of one or more wireless interfaces, such as IEEE 802.11 (Wifi), BLUETOOTH®, global positioning system (GPS), or a wide-area wireless interface. However, other forms of physical layer interfaces and other types of standard or proprietary communication protocols may be used over network interface 106. Furthermore, network interface 106 may comprise multiple physical interfaces. For instance, some embodiments of computing device 100 may include Ethernet, BLUETOOTH®, and Wifi interfaces.

Input/output unit 108 may facilitate user and peripheral device interaction with computing device 100. Input/output unit 108 may include one or more types of input devices, such as a keyboard, a mouse, a touch screen, and so on. Similarly, input/output unit 108 may include one or more types of output devices, such as a screen, monitor, printer, and/or one or more light emitting diodes (LEDs). Additionally or alternatively, computing device 100 may communicate with other devices using a universal serial bus (USB) or high-definition multimedia interface (HDMI) port interface, for example.

In some embodiments, one or more computing devices like computing device 100 may be deployed to support an aPaaS architecture. The exact physical location, connectivity, and configuration of these computing devices may be unknown and/or unimportant to client devices. Accordingly, the computing devices may be referred to as "cloud-based" devices that may be housed at various remote data center locations.

Figure 2:
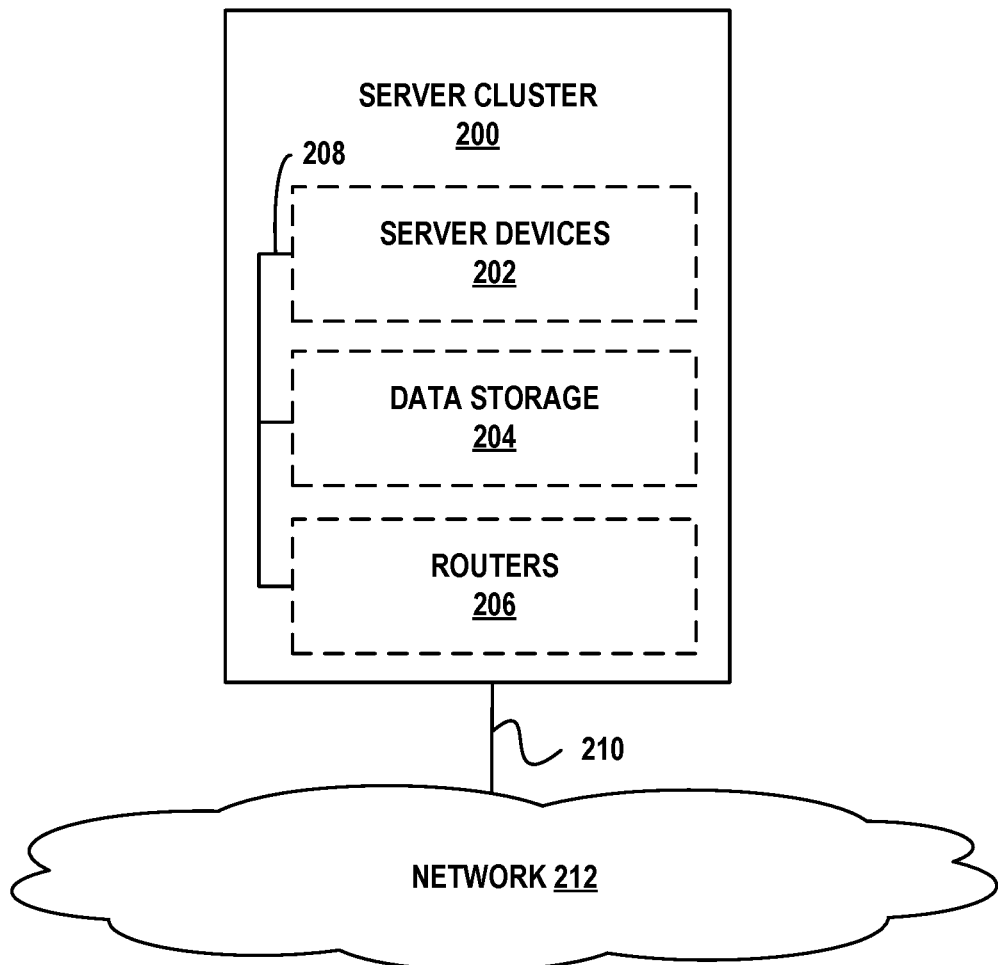
FIG. 2 illustrates a schematic drawing of a server device cluster, in accordance with example embodiments.

FIG. 2 depicts a cloud-based server cluster 200 in accordance with example embodiments. In FIG. 2, operations of a computing device (e.g., computing device 100) may be distributed between server devices 202, data storage 204, and routers 206, all of which may be connected by local cluster network 208. The number of server devices 202, data storages 204, and routers 206 in server cluster 200 may depend on the computing task(s) and/or applications assigned to server cluster 200.

For example, server devices 202 can be configured to perform various computing tasks of computing device 100. Thus, computing tasks can be distributed among one or more of server devices 202. To the extent that these computing tasks can be performed in parallel, such a distribution of tasks may reduce the total time to complete these tasks and return a result. For purposes of simplicity, both server cluster 200 and individual server devices 202 may be referred to as a "server device." This nomenclature should be understood to imply that one or more distinct server devices, data storage devices, and cluster routers may be involved in server device operations.

Data storage 204 may be data storage arrays that include drive array controllers configured to manage read and write access to groups of hard disk drives and/or solid state drives. The drive array controllers, alone or in conjunction with server devices 202, may also be configured to manage backup or redundant copies of the data stored in data storage 204 to protect against drive failures or other types of failures that prevent one or more of server devices 202 from accessing units of data storage 204. Other types of memory aside from drives may be used.

Routers 206 may include networking equipment configured to provide internal and external communications for server cluster 200. For example, routers 206 may include one or more packet-switching and/or routing devices (including switches and/or gateways) configured to provide (i) network communications between server devices 202 and data storage 204 via local cluster network 208, and/or (ii) network communications between server cluster 200 and other devices via communication link 210 to network 212.

Additionally, the configuration of routers 206 can be based at least in part on the data communication requirements of server devices 202 and data storage 204, the latency and throughput of the local cluster network 208, the latency, throughput, and cost of communication link 210, and/or other factors that may contribute to the cost, speed, fault-tolerance, resiliency, efficiency, and/or other design goals of the system architecture.

As a possible example, data storage 204 may include any form of database, such as a structured query language (SQL) database. Various types of data structures may store the information in such a database, including but not limited to tables, arrays, lists, trees, and tuples. Furthermore, any databases in data storage 204 may be monolithic or distributed across multiple physical devices.

Server devices 202 may be configured to transmit data to and receive data from data storage 204. This transmission and retrieval may take the form of SQL queries or other types of database queries, and the output of such queries, respectively. Additional text, images, video, and/or audio may be included as well. Furthermore, server devices 202 may organize the received data into web page or web application representations. Such a representation may take the form of a markup language, such as the hypertext markup language (HTML), the extensible markup language (XML), or some other standardized or proprietary format. Moreover, server devices 202 may have the capability of executing various types of computerized scripting languages, such as but not limited to Perl, Python, PHP Hypertext Preprocessor (PHP), Active Server Pages (ASP), JAVASCRIPT®, and so on. Computer program code written in these languages may facilitate the providing of web pages to client devices, as well as client device interaction with the web pages. Alternatively or additionally, JAVA® may be used to facilitate generation of web pages and/or to provide web application functionality.

III. Example Remote Network Management Architecture

Figure 3:
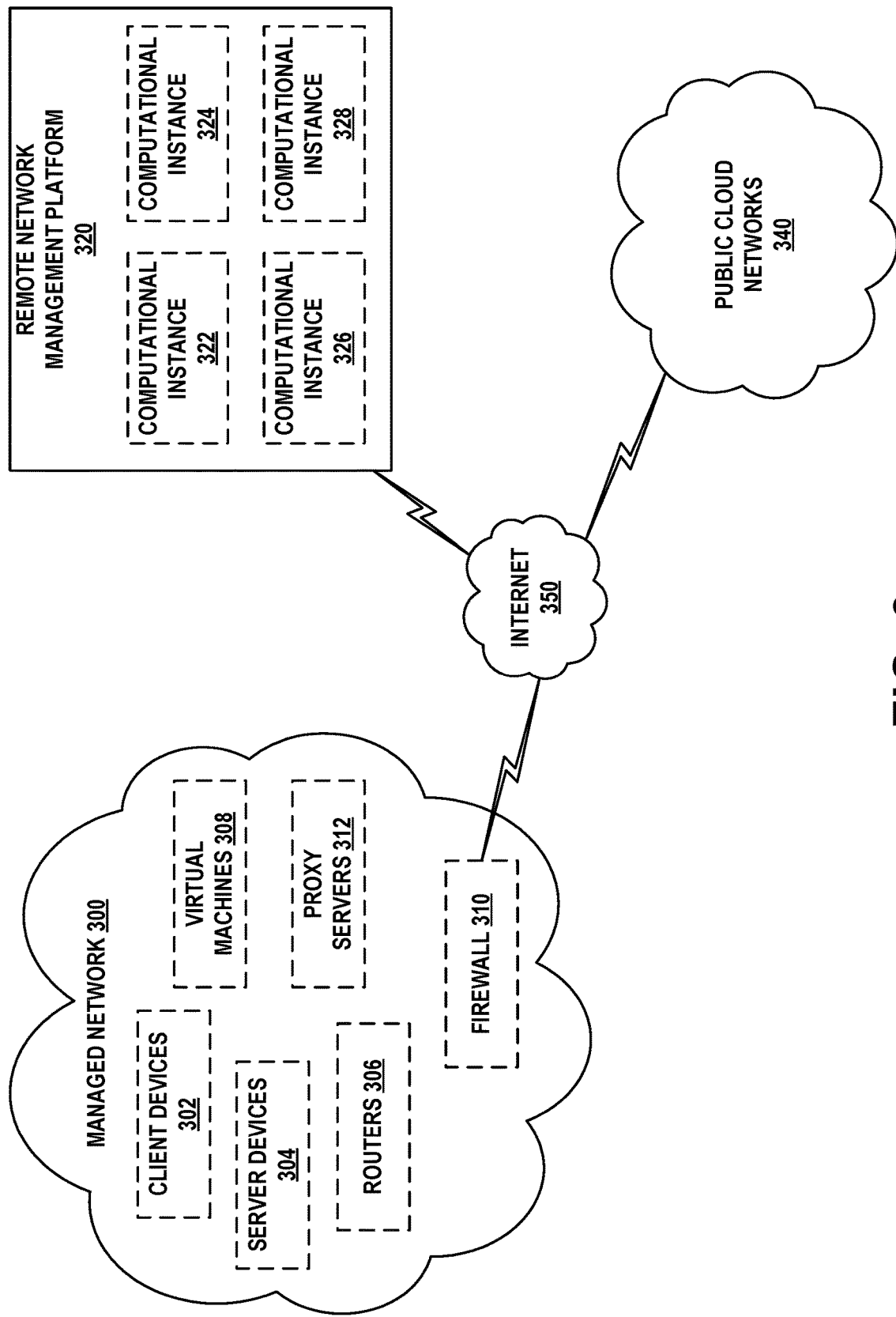
FIG. 3 depicts a remote network management architecture, in accordance with example embodiments.

FIG. 3 depicts a remote network management architecture, in accordance with example embodiments. This architecture includes three main components—managed network 300, remote network management platform 320, and public cloud networks 340—all connected by way of Internet 350.

A. Managed Networks

Managed network 300 may be, for example, an enterprise network used by an entity for computing and communications tasks, as well as storage of data. Thus, managed network 300 may include client devices 302, server devices 304, routers 306, virtual machines 308, firewall 310, and/or proxy servers 312. Client devices 302 may be embodied by computing device 100, server devices 304 may be embodied by computing device 100 or server cluster 200, and routers 306 may be any type of router, switch, or gateway.

Virtual machines 308 may be embodied by one or more of computing device 100 or server cluster 200. In general, a virtual machine is an emulation of a computing system, and mimics the functionality (e.g., processor, memory, and communication resources) of a physical computer. One physical computing system, such as server cluster 200, may support up to thousands of individual virtual machines. In some embodiments, virtual machines 308 may be managed by a centralized server device or application that facilitates allocation of physical computing resources to individual virtual machines, as well as performance and error reporting. Enterprises often employ virtual machines in order to allocate computing resources in an efficient, as needed fashion. Providers of virtualized computing systems include VMWARE® and MICROSOFT®.

Firewall 310 may be one or more specialized routers or server devices that protect managed network 300 from unauthorized attempts to access the devices, applications, and services therein, while allowing authorized communication that is initiated from managed network 300. Firewall 310 may also provide intrusion detection, web filtering, virus scanning, application-layer gateways, and other applications or services. In some embodiments not shown in FIG. 3, managed network 300 may include one or more virtual private network (VPN) gateways with which it communicates with remote network management platform 320 (see below).

Managed network 300 may also include one or more proxy servers 312. An embodiment of proxy servers 312 may be a server application that facilitates communication and movement of data between managed network 300, remote network management platform 320, and public cloud networks 340. In particular, proxy servers 312 may be able to establish and maintain secure communication sessions with one or more computational instances of remote network management platform 320. By way of such a session, remote network management platform 320 may be able to discover and manage aspects of the architecture and configuration of managed network 300 and its components. Possibly with the assistance of proxy servers 312, remote network management platform 320 may also be able to discover and manage aspects of public cloud networks 340 that are used by managed network 300.

Firewalls, such as firewall 310, typically deny all communication sessions that are incoming by way of Internet 350, unless such a session was ultimately initiated from behind the firewall (i.e., from a device on managed network 300) or the firewall has been explicitly configured to support the session. By placing proxy servers 312 behind firewall 310 (e.g., within managed network 300 and protected by firewall 310), proxy servers 312 may be able to initiate these communication sessions through firewall 310. Thus, firewall 310 might not have to be specifically configured to support incoming sessions from remote network management platform 320, thereby avoiding potential security risks to managed network 300.

In some cases, managed network 300 may consist of a few devices and a small number of networks. In other deployments, managed network 300 may span multiple physical locations and include hundreds of networks and hundreds of thousands of devices. Thus, the architecture depicted in FIG. 3 is capable of scaling up or down by orders of magnitude.

Furthermore, depending on the size, architecture, and connectivity of managed network 300, a varying number of proxy servers 312 may be deployed therein. For example, each one of proxy servers 312 may be responsible for communicating with remote network management platform 320 regarding a portion of managed network 300. Alternatively or additionally, sets of two or more proxy servers may be assigned to such a portion of managed network 300 for purposes of load balancing, redundancy, and/or high availability.

B. Remote Network Management Platforms

Remote network management platform 320 is a hosted environment that provides aPaaS services to users, particularly to the operator of managed network 300. These services may take the form of web-based portals, for example, using the aforementioned web-based technologies. Thus, a user can securely access remote network management platform 320 from, for example, client devices 302, or potentially from a client device outside of managed network 300. By way of the web-based portals, users may design, test, and deploy applications, generate reports, view analytics, and perform other tasks.

As shown in FIG. 3, remote network management platform 320 includes four computational instances 322, 324, 326, and 328. Each of these computational instances may represent one or more server nodes operating dedicated copies of the aPaaS software and/or one or more database nodes. The arrangement of server and database nodes on physical server devices and/or virtual machines can be flexible and may vary based on enterprise needs. In combination, these nodes may provide a set of web portals, services, and applications (e.g., a wholly-functioning aPaaS system) available to a particular enterprise. In some cases, a single enterprise may use multiple computational instances.

For example, managed network 300 may be an enterprise customer of remote network management platform 320, and may use computational instances 322, 324, and 326. The reason for providing multiple computational instances to one customer is that the customer may wish to independently develop, test, and deploy its applications and services. Thus, computational instance 322 may be dedicated to application development related to managed network 300, computational instance 324 may be dedicated to testing these applications, and computational instance 326 may be dedicated to the live operation of tested applications and services. A computational instance may also be referred to as a hosted instance, a remote instance, a customer instance, or by some other designation. Any application deployed onto a computational instance may be a scoped application, in that its access to databases within the computational instance can be restricted to certain elements therein (e.g., one or more particular database tables or particular rows within one or more database tables).

For purposes of clarity, the disclosure herein refers to the arrangement of application nodes, database nodes, aPaaS software executing thereon, and underlying hardware as a "computational instance." Note that users may colloquially refer to the graphical user interfaces provided thereby as "instances." But unless it is defined otherwise herein, a "computational instance" is a computing system disposed within remote network management platform 320.

The multi-instance architecture of remote network management platform 320 is in contrast to conventional multi-tenant architectures, over which multi-instance architectures exhibit several advantages. In multi-tenant architectures, data from different customers (e.g., enterprises) are comingled in a single database. While these customers' data are separate from one another, the separation is enforced by the software that operates the single database. As a consequence, a security breach in this system may impact all customers' data, creating additional risk, especially for entities subject to governmental, healthcare, and/or financial regulation. Furthermore, any database operations that impact one customer will likely impact all customers sharing that database. Thus, if there is an outage due to hardware or software errors, this outage affects all such customers. Likewise, if the database is to be upgraded to meet the needs of one customer, it will be unavailable to all customers during the upgrade process. Often, such maintenance windows will be long, due to the size of the shared database.

In contrast, the multi-instance architecture provides each customer with its own database in a dedicated computing instance. This prevents comingling of customer data, and allows each instance to be independently managed. For example, when one customer's instance experiences an outage due to errors or an upgrade, other computational instances are not impacted. Maintenance down time is limited because the database only contains one customer's data. Further, the simpler design of the multi-instance architecture allows redundant copies of each customer database and instance to be deployed in a geographically diverse fashion. This facilitates high availability, where the live version of the customer's instance can be moved when faults are detected or maintenance is being performed.

In some embodiments, remote network management platform 320 may include one or more central instances, controlled by the entity that operates this platform. Like a computational instance, a central instance may include some number of application and database nodes disposed upon some number of physical server devices or virtual machines. Such a central instance may serve as a repository for specific configurations of computational instances as well as data that can be shared amongst at least some of the computational instances. For instance, definitions of common security threats that could occur on the computational instances, software packages that are commonly discovered on the computational instances, and/or an application store for applications that can be deployed to the computational instances may reside in a central instance. Computational instances may communicate with central instances by way of well-defined interfaces in order to obtain this data.

In order to support multiple computational instances in an efficient fashion, remote network management platform 320 may implement a plurality of these instances on a single hardware platform. For example, when the aPaaS system is implemented on a server cluster such as server cluster 200, it may operate virtual machines that dedicate varying amounts of computational, storage, and communication resources to instances. But full virtualization of server cluster 200 might not be necessary, and other mechanisms may be used to separate instances. In some examples, each instance may have a dedicated account and one or more dedicated databases on server cluster 200. Alternatively, a computational instance such as computational instance 322 may span multiple physical devices.

In some cases, a single server cluster of remote network management platform 320 may support multiple independent enterprises. Furthermore, as described below, remote network management platform 320 may include multiple server clusters deployed in geographically diverse data centers in order to facilitate load balancing, redundancy, and/or high availability.

C. Public Cloud Networks

Public cloud networks 340 may be remote server devices (e.g., a plurality of server clusters such as server cluster 200) that can be used for outsourced computation, data storage, communication, and service hosting operations. These servers may be virtualized (i.e., the servers may be virtual machines). Examples of public cloud networks 340 may include AMAZON WEB SERVICES® and MICROSOFT® AZURE®. Like remote network management platform 320, multiple server clusters supporting public cloud networks 340 may be deployed at geographically diverse locations for purposes of load balancing, redundancy, and/or high availability.

Managed network 300 may use one or more of public cloud networks 340 to deploy applications and services to its clients and customers. For instance, if managed network 300 provides online music streaming services, public cloud networks 340 may store the music files and provide web interface and streaming capabilities. In this way, the enterprise of managed network 300 does not have to build and maintain its own servers for these operations.

Remote network management platform 320 may include modules that integrate with public cloud networks 340 to expose virtual machines and managed services therein to managed network 300. The modules may allow users to request virtual resources, discover allocated resources, and provide flexible reporting for public cloud networks 340. In order to establish this functionality, a user from managed network 300 might first establish an account with public cloud networks 340, and request a set of associated resources. Then, the user may enter the account information into the appropriate modules of remote network management platform 320. These modules may then automatically discover the manageable resources in the account, and also provide reports related to usage, performance, and billing.

D. Communication Support and Other Operations

Internet 350 may represent a portion of the global Internet. However, Internet 350 may alternatively represent a different type of network, such as a private wide-area or local-area packet-switched network.

Figure 4:
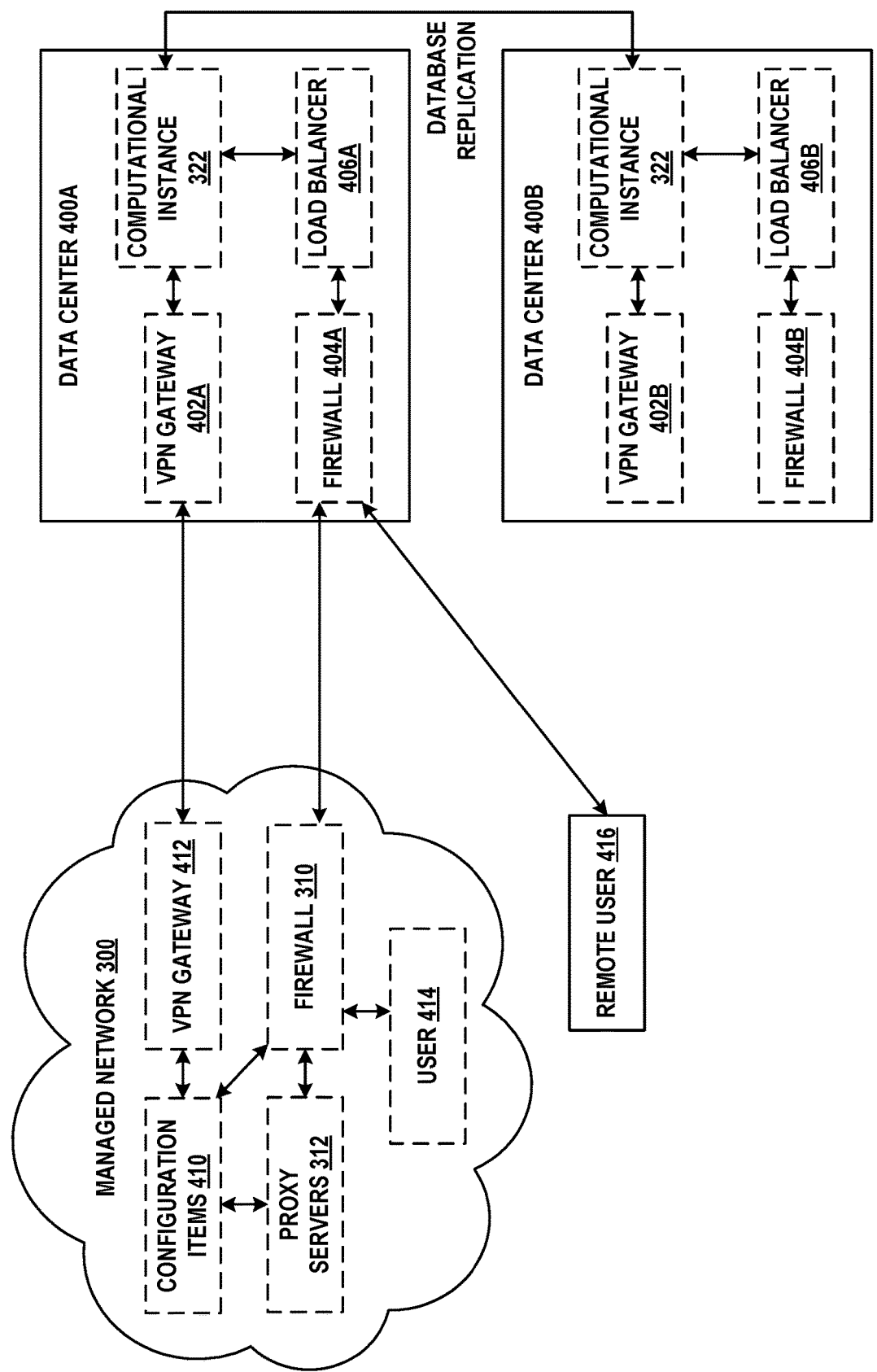
FIG. 4 depicts a communication environment involving a remote network management architecture, in accordance with example embodiments.

FIG. 4 further illustrates the communication environment between managed network 300 and computational instance 322, and introduces additional features and alternative embodiments. In FIG. 4, computational instance 322 is replicated across data centers 400A and 400B. These data centers may be geographically distant from one another, perhaps in different cities or different countries. Each data center includes support equipment that facilitates communication with managed network 300, as well as remote users.

In data center 400A, network traffic to and from external devices flows either through VPN gateway 402A or firewall 404A. VPN gateway 402A may be peered with VPN gateway 412 of managed network 300 by way of a security protocol such as Internet Protocol Security (IPSEC) or Transport Layer Security (TLS). Firewall 404A may be configured to allow access from authorized users, such as user 414 and remote user 416, and to deny access to unauthorized users. By way of firewall 404A, these users may access computational instance 322, and possibly other computational instances. Load balancer 406A may be used to distribute traffic amongst one or more physical or virtual server devices that host computational instance 322. Load balancer 406A may simplify user access by hiding the internal configuration of data center 400A, (e.g., computational instance 322) from client devices. For instance, if computational instance 322 includes multiple physical or virtual computing devices that share access to multiple databases, load balancer 406A may distribute network traffic and processing tasks across these computing devices and databases so that no one computing device or database is significantly busier than the others. In some embodiments, computational instance 322 may include VPN gateway 402A, firewall 404A, and load balancer 406A.

Data center 400B may include its own versions of the components in data center 400A. Thus, VPN gateway 402B, firewall 404B, and load balancer 406B may perform the same or similar operations as VPN gateway 402A, firewall 404A, and load balancer 406A, respectively. Further, by way of real-time or near-real-time database replication and/or other operations, computational instance 322 may exist simultaneously in data centers 400A and 400B.

Data centers 400A and 400B as shown in FIG. 4 may facilitate redundancy and high availability. In the configuration of FIG. 4, data center 400A is active and data center 400B is passive. Thus, data center 400A is serving all traffic to and from managed network 300, while the version of computational instance 322 in data center 400B is being updated in near-real-time. Other configurations, such as one in which both data centers are active, may be supported.

Should data center 400A fail in some fashion or otherwise become unavailable to users, data center 400B can take over as the active data center. For example, domain name system (DNS) servers that associate a domain name of computational instance 322 with one or more Internet Protocol (IP) addresses of data center 400A may re-associate the domain name with one or more IP addresses of data center 400B. After this re-association completes (which may take less than one second or several seconds), users may access computational instance 322 by way of data center 400B.

FIG. 4 also illustrates a possible configuration of managed network 300. As noted above, proxy servers 312 and user 414 may access computational instance 322 through firewall 310. Proxy servers 312 may also access configuration items 410. In FIG. 4, configuration items 410 may refer to any or all of client devices 302, server devices 304, routers 306, and virtual machines 308, any applications or services executing thereon, as well as relationships between devices, applications, and services. Thus, the term "configuration items" may be shorthand for any physical or virtual device, or any application or service remotely discoverable or managed by computational instance 322, or relationships between discovered devices, applications, and services. Configuration items may be represented in a configuration management database (CMDB) of computational instance 322.

As noted above, VPN gateway 412 may provide a dedicated VPN to VPN gateway 402A. Such a VPN may be helpful when there is a significant amount of traffic between managed network 300 and computational instance 322, or security policies otherwise suggest or require use of a VPN between these sites. In some embodiments, any device in managed network 300 and/or computational instance 322 that directly communicates via the VPN is assigned a public IP address. Other devices in managed network 300 and/or computational instance 322 may be assigned private IP addresses (e.g., IP addresses selected from the 10.0.0.0-10.255.255.255 or 192.168.0.0-192.168.255.255 ranges, represented in shorthand as subnets 10.0.0.0/8 and 192.168.0.0/16, respectively).

IV. Example Device, Application, and Service Discovery

In order for remote network management platform 320 to administer the devices, applications, and services of managed network 300, remote network management platform 320 may first determine what devices are present in managed network 300, the configurations and operational statuses of these devices, and the applications and services provided by the devices, as well as the relationships between discovered devices, applications, and services. As noted above, each device, application, service, and relationship may be referred to as a configuration item. The process of defining configuration items within managed network 300 is referred to as discovery, and may be facilitated at least in part by proxy servers 312.

For purposes of the embodiments herein, an "application" may refer to one or more processes, threads, programs, client modules, server modules, or any other software that executes on a device or group of devices. A "service" may refer to a high-level capability provided by multiple applications executing on one or more devices working in conjunction with one another. For example, a high-level web service may involve multiple web application server threads executing on one device and accessing information from a database application that executes on another device.

Figure 5A:
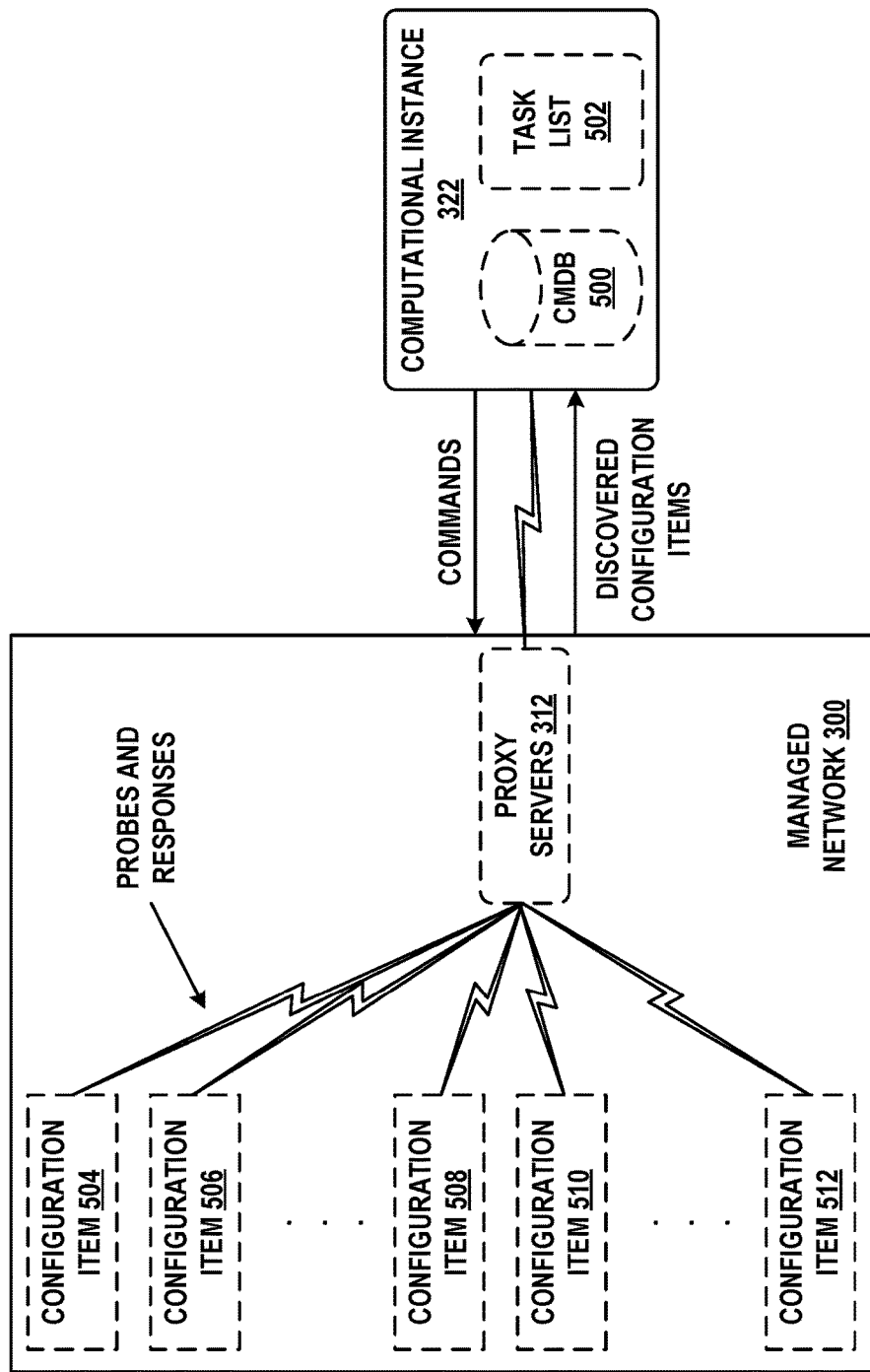
FIG. 5A depicts another communication environment involving a remote network management architecture, in accordance with example embodiments.

FIG. 5A provides a logical depiction of how configuration items can be discovered, as well as how information related to discovered configuration items can be stored. For sake of simplicity, remote network management platform 320, public cloud networks 340, and Internet 350 are not shown.

In FIG. 5A, CMDB 500 and task list 502 are stored within computational instance 322. Computational instance 322 may transmit discovery commands to proxy servers 312. In response, proxy servers 312 may transmit probes to various devices, applications, and services in managed network 300. These devices, applications, and services may transmit responses to proxy servers 312, and proxy servers 312 may then provide information regarding discovered configuration items to CMDB 500 for storage therein. Configuration items stored in CMDB 500 represent the environment of managed network 300.

Task list 502 represents a list of activities that proxy servers 312 are to perform on behalf of computational instance 322. As discovery takes place, task list 502 is populated. Proxy servers 312 repeatedly query task list 502, obtain the next task therein, and perform this task until task list 502 is empty or another stopping condition has been reached.

To facilitate discovery, proxy servers 312 may be configured with information regarding one or more subnets in managed network 300 that are reachable by way of proxy servers 312. For instance, proxy servers 312 may be given the IP address range 192.168.0/24 as a subnet. Then, computational instance 322 may store this information in CMDB 500 and place tasks in task list 502 for discovery of devices at each of these addresses.

FIG. 5A also depicts devices, applications, and services in managed network 300 as configuration items 504, 506, 508, 510, and 512. As noted above, these configuration items represent a set of physical and/or virtual devices (e.g., client devices, server devices, routers, or virtual machines), applications executing thereon (e.g., web servers, email servers, databases, or storage arrays), relationships therebetween, as well as services that involve multiple individual configuration items.

Placing the tasks in task list 502 may trigger or otherwise cause proxy servers 312 to begin discovery. Alternatively or additionally, discovery may be manually triggered or automatically triggered based on triggering events (e.g., discovery may automatically begin once per day at a particular time).

In general, discovery may proceed in four logical phases: scanning, classification, identification, and exploration. Each phase of discovery involves various types of probe messages being transmitted by proxy servers 312 to one or more devices in managed network 300. The responses to these probes may be received and processed by proxy servers 312, and representations thereof may be transmitted to CMDB 500. Thus, each phase can result in more configuration items being discovered and stored in CMDB 500.

In the scanning phase, proxy servers 312 may probe each IP address in the specified range of IP addresses for open Transmission Control Protocol (TCP) and/or User Datagram Protocol (UDP) ports to determine the general type of device. The presence of such open ports at an IP address may indicate that a particular application is operating on the device that is assigned the IP address, which in turn may identify the operating system used by the device. For example, if TCP port 135 is open, then the device is likely executing a WINDOWS® operating system. Similarly, if TCP port 22 is open, then the device is likely executing a UNIX® operating system, such as LINUX®. If UDP port 161 is open, then the device may be able to be further identified through the Simple Network Management Protocol (SNMP). Other possibilities exist. Once the presence of a device at a particular IP address and its open ports have been discovered, these configuration items are saved in CMDB 500.

In the classification phase, proxy servers 312 may further probe each discovered device to determine the version of its operating system. The probes used for a particular device are based on information gathered about the devices during the scanning phase. For example, if a device is found with TCP port 22 open, a set of UNIX®-specific probes may be used. Likewise, if a device is found with TCP port 135 open, a set of WINDOWS®-specific probes may be used. For either case, an appropriate set of tasks may be placed in task list 502 for proxy servers 312 to carry out. These tasks may result in proxy servers 312 logging on, or otherwise accessing information from the particular device. For instance, if TCP port 22 is open, proxy servers 312 may be instructed to initiate a Secure Shell (SSH) connection to the particular device and obtain information about the operating system thereon from particular locations in the file system. Based on this information, the operating system may be determined. As an example, a UNIX® device with TCP port 22 open may be classified as AIX®, HPUX, LINUX®, MACOS®, or SOLARIS®. This classification information may be stored as one or more configuration items in CMDB 500.

In the identification phase, proxy servers 312 may determine specific details about a classified device. The probes used during this phase may be based on information gathered about the particular devices during the classification phase. For example, if a device was classified as LINUX®, a set of LINUX®-specific probes may be used. Likewise, if a device was classified as WINDOWS® 2012, as a set of WINDOWS®-2012-specific probes may be used. As was the case for the classification phase, an appropriate set of tasks may be placed in task list 502 for proxy servers 312 to carry out. These tasks may result in proxy servers 312 reading information from the particular device, such as basic input/output system (BIOS) information, serial numbers, network interface information, media access control address(es) assigned to these network interface(s), IP address(es) used by the particular device and so on. This identification information may be stored as one or more configuration items in CMDB 500.

In the exploration phase, proxy servers 312 may determine further details about the operational state of a classified device. The probes used during this phase may be based on information gathered about the particular devices during the classification phase and/or the identification phase. Again, an appropriate set of tasks may be placed in task list 502 for proxy servers 312 to carry out. These tasks may result in proxy servers 312 reading additional information from the particular device, such as processor information, memory information, lists of running processes (applications), and so on. Once more, the discovered information may be stored as one or more configuration items in CMDB 500.

Running discovery on a network device, such as a router, may utilize SNMP. Instead of or in addition to determining a list of running processes or other application-related information, discovery may determine additional subnets known to the router and the operational state of the router's network interfaces (e.g., active, inactive, queue length, number of packets dropped, etc.). The IP addresses of the additional subnets may be candidates for further discovery procedures. Thus, discovery may progress iteratively or recursively.

Once discovery completes, a snapshot representation of each discovered device, application, and service is available in CMDB 500. For example, after discovery, operating system version, hardware configuration, and network configuration details for client devices, server devices, and routers in managed network 300, as well as applications executing thereon, may be stored. This collected information may be presented to a user in various ways to allow the user to view the hardware composition and operational status of devices, as well as the characteristics of services that span multiple devices and applications.

Furthermore, CMDB 500 may include entries regarding dependencies and relationships between configuration items. More specifically, an application that is executing on a particular server device, as well as the services that rely on this application, may be represented as such in CMDB 500. For example, suppose that a database application is executing on a server device, and that this database application is used by a new employee onboarding service as well as a payroll service. Thus, if the server device is taken out of operation for maintenance, it is clear that the employee onboarding service and payroll service will be impacted. Likewise, the dependencies and relationships between configuration items may be able to represent the services impacted when a particular router fails.

In general, dependencies and relationships between configuration items may be displayed on a web-based interface and represented in a hierarchical fashion. Thus, adding, changing, or removing such dependencies and relationships may be accomplished by way of this interface.

Furthermore, users from managed network 300 may develop workflows that allow certain coordinated activities to take place across multiple discovered devices. For instance, an IT workflow might allow the user to change the common administrator password to all discovered LINUX® devices in a single operation.

In order for discovery to take place in the manner described above, proxy servers 312, CMDB 500, and/or one or more credential stores may be configured with credentials for one or more of the devices to be discovered. Credentials may include any type of information needed in order to access the devices. These may include userid/password pairs, certificates, and so on. In some embodiments, these credentials may be stored in encrypted fields of CMDB 500. Proxy servers 312 may contain the decryption key for the credentials so that proxy servers 312 can use these credentials to log on to or otherwise access devices being discovered.

Figure 5B:
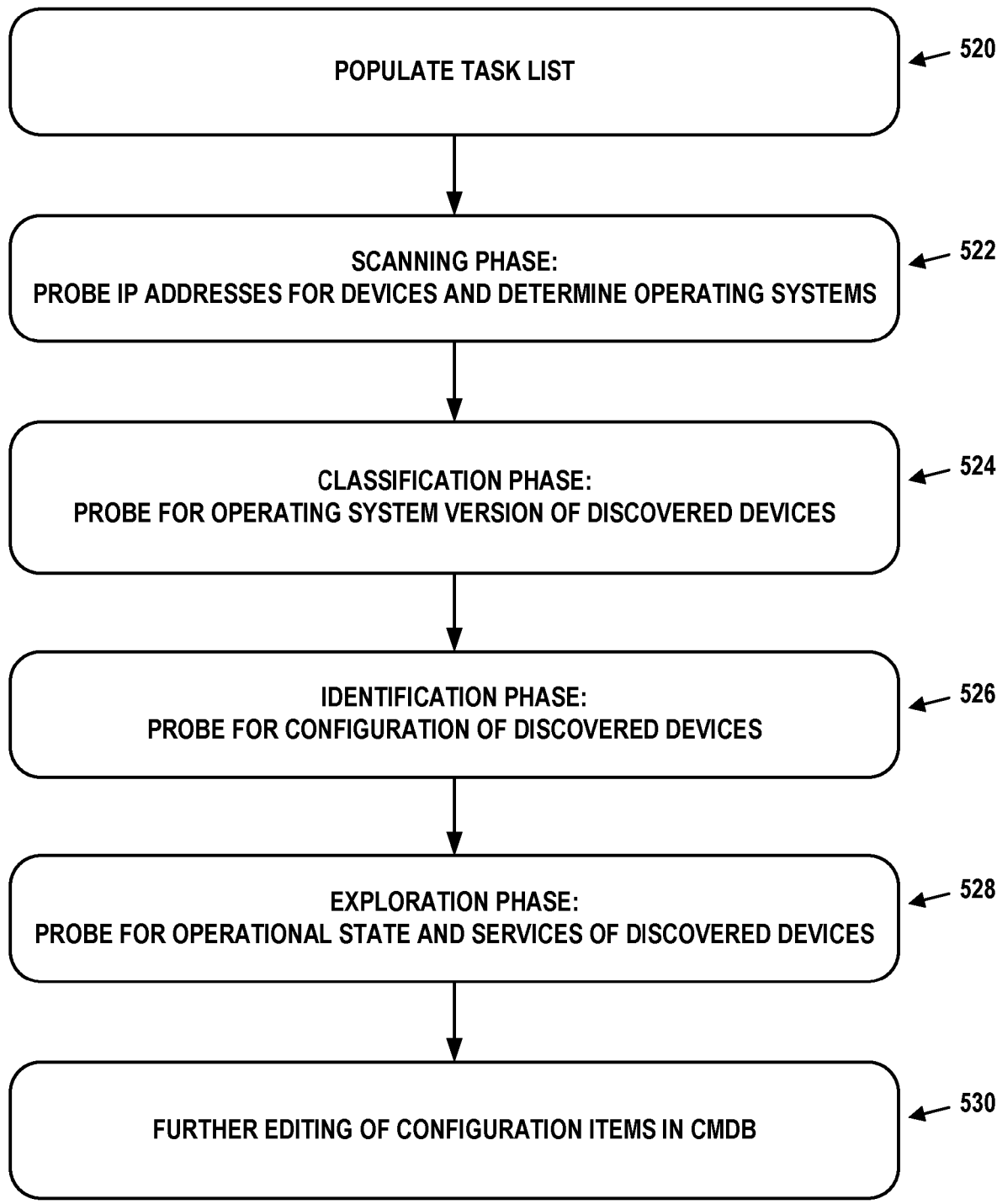
FIG. 5B is a flow chart, in accordance with example embodiments.

The discovery process is depicted as a flow chart in FIG. 5B. At block 520, the task list in the computational instance is populated, for instance, with a range of IP addresses. At block 522, the scanning phase takes place. Thus, the proxy servers probe the IP addresses for devices using these IP addresses, and attempt to determine the operating systems that are executing on these devices. At block 524, the classification phase takes place. The proxy servers attempt to determine the operating system version of the discovered devices. At block 526, the identification phase takes place. The proxy servers attempt to determine the hardware and/or software configuration of the discovered devices. At block 528, the exploration phase takes place. The proxy servers attempt to determine the operational state and applications executing on the discovered devices. At block 530, further editing of the configuration items representing the discovered devices and applications may take place. This editing may be automated and/or manual in nature.

The blocks represented in FIG. 5B are examples. Discovery may be a highly configurable procedure that can have more or fewer phases, and the operations of each phase may vary. In some cases, one or more phases may be customized, or may otherwise deviate from the exemplary descriptions above.

In this manner, a remote network management platform may discover and inventory the hardware, software, and services deployed on and provided by the managed network. As noted above, this data may be stored in a CMDB of the associated computational instance as configuration items. For example, individual hardware components (e.g., computing devices, virtual servers, databases, routers, etc.) may be represented as hardware configuration items, while the applications installed and/or executing thereon may be represented as software configuration items.

The relationship between a software configuration item installed or executing on a hardware configuration item may take various forms, such as "is hosted on", "runs on", or "depends on". Thus, a database application installed on a server device may have the relationship "is hosted on" with the server device to indicate that the database application is hosted on the server device. In some embodiments, the server device may have a reciprocal relationship of "used by" with the database application to indicate that the server device is used by the database application. These relationships may be automatically found using the discovery procedures described above, though it is possible to manually set relationships as well.

The relationship between a service and one or more software configuration items may also take various forms. As an example, a web service may include a web server software configuration item and a database application software configuration item, each installed on different hardware configuration items. The web service may have a "depends on" relationship with both of these software configuration items, while the software configuration items have a "used by" reciprocal relationship with the web service. Services might not be able to be fully determined by discovery procedures, and instead may rely on service mapping (e.g., probing configuration files and/or carrying out network traffic analysis to determine service level relationships between configuration items) and possibly some extent of manual configuration.

Regardless of how relationship information is obtained, it can be valuable for the operation of a managed network. Notably, IT personnel can quickly determine where certain software applications are deployed, and what configuration items make up a service. This allows for rapid pinpointing of root causes of service outages or degradation. For example, if two different services are suffering from slow response times, the CMDB can be queried (perhaps among other activities) to determine that the root cause is a database application that is used by both services having high processor utilization. Thus, IT personnel can address the database application rather than waste time considering the health and performance of other configuration items that make up the services.

V. Example Contact Tracing Mechanisms

The embodiments herein provide a way to perform contact tracing amongst users who may need to be in physical proximity of one another, such as employees of an enterprise. Such a capability can be of critical importance in the presence of a communicable disease, especially one with a high transmission rate and long incubation period. As an example, the COVID-19 virus outbreak that began in late 2019 and early 2020 became a pandemic due to its ability to quickly spread person-to-person within a community. But the spread of other pathogens, such as influenza or even the common cold, may be mitigated through contact tracing and sub sequent self-quarantine or isolation.

These embodiments provide semi-automated or fully-automated mechanisms for anonymously tracking contacts between users. When one of these users reports that he or she is subject to an adverse condition (e.g., is symptomatic, has tested positive for a pathogen, or may have been exposed to a pathogen), the mechanisms herein can identify other users who were in proximity to this user within a pre-determined period of time, and proactively notify those users that they are at risk of having been infected. The enterprise may then instruct the notified users to self-quarantine by working from home or otherwise not reporting in person to enterprise premises.

Further rounds of second-order contact tracing for the contacts of the user's contacts, third-order contact tracing for the contacts of the contacts of the user's contacts, and so on may also take place in an iterative or recursive fashion. Thus, from a web of recorded contacts amongst a group of users, a contact tracing tree of up to a predefined depth can be generated with an initial user who reported the adverse condition at the root. Any user in this contact tracing tree may be subject to notification and/or quarantine.

Further, these embodiments address many privacy concerns of users and enterprises by only identifying contacts between users on an as needed basis, and maintaining contact data in a distributed fashion. Thus, unless and until a user reports an adverse condition, no one individual may have access to the full extent of contact tracing data. Further, the data used to generate contact tracing trees, as well as these trees themselves, may be stored in a secure fashion (e.g., encrypted) so that it can only be accessed by a small number of trusted administrative users in the enterprise.

A. Architecture

Figure 6:
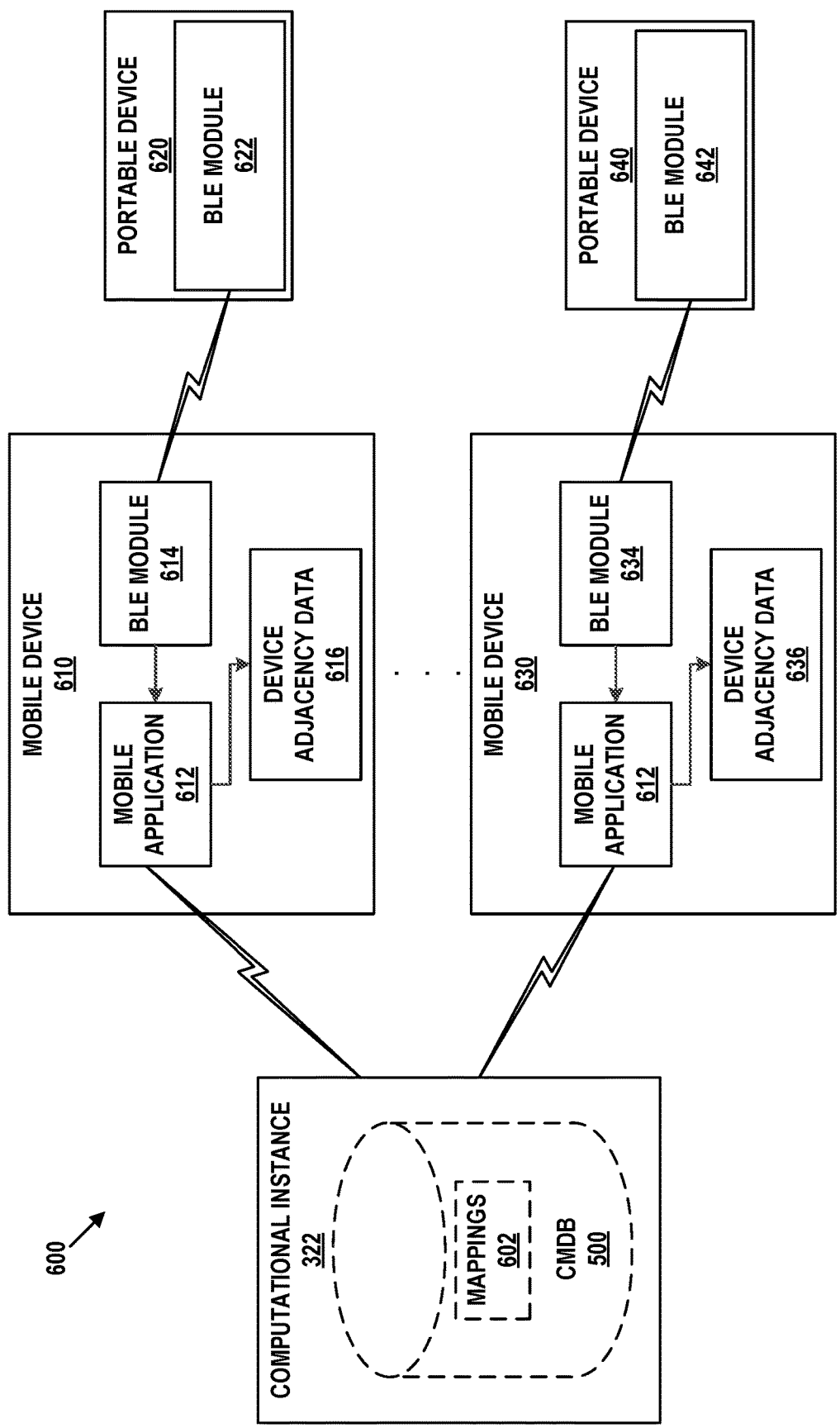
FIG. 6 is an architecture for contact tracing, in accordance with example embodiments.

FIG. 6 depicts architecture 600 for contact tracing. An enterprise may employ computational instance 322 of remote network management platform 320. Various types of users may be associated with the enterprise, such as employees, contractors, vendors, and so on (all of which may be referred to herein as "employees" or "users" for sake of convenience). These users may each possess a mobile device, such as mobile devices 610 and 630. The mobile devices may be, for example, cellular phones, smartphones, tablets, and/or laptop computers and may be owned by the employees or issued to the employees by the enterprise. Users who work at least part of the time on the premises of the enterprise (e.g., in a physical office of the enterprise) may also be issued portable devices, such as portable devices 620 and 640. Such portable devices may be distributed users during times when pathogens are particularly prevalent and/or when contact tracing of the spread of a potential pathogen is desirable. Architecture 600 is just one example of a physical arrangement that can facilitate contact tracing. Other possibilities exist.

Computational instance 322 may include CMDB 500 as described above, and CMDB 500 may store mappings 602 in one or more database tables, for example. Mappings 602 may be pairwise associations between user identifiers of enterprise users and portable device identifiers of the portable devices issued to these users. For example, if a user with user identifier X is issued a portable device with portable device identifier Y, mappings 602 may contain an association between X and Y. These associations may be manually entered into CMDB 500, or (as described in more detail below) automatically generated. In some embodiments, mappings 602 may be encrypted in the interest of privacy. Also, mappings 602 could exist in a database other than CMDB 500.

Mobile device 610 may be capable of communicating with computational instance 322 by way of local area networks (e.g., Wifi) or wide-area networks (e.g., cellular). Mobile device 610 is capable of communicating with portable device 620 by way of BLUETOOTH® Low Energy (BLE) using BLE module 614, but other types of wireless personal-area networking technologies can be used in place of BLE. In any event, it is assumed that portable device 620 was issued to the user who possesses mobile device 610, that mobile device 610 and portable device 620 have been paired, and that mappings 602 has been updated to reflect this pairing. An example pairing process is described below. Mobile device 610 may also have installed or otherwise disposed upon it mobile application 612 and device adjacency data 616, both of which can be used to facilitate contact tracing.

Similar to mobile device 610, mobile device 630 may be capable of communicating with computational instance 322 by way of local area networks or wide-area networks. Mobile device 630 may also be capable of communicating with portable device 640 by way of BLE using BLE module 634. Thus, it may be assumed that portable device 640 was issued to the user who possesses mobile device 630, that mobile device 630 and portable device 640 have been paired, and that mappings 602 has been updated to reflect this pairing. Mobile device 630 may also have installed or otherwise disposed upon it mobile application 612 and device adjacency data 636, both of which can be used to facilitate contact tracing.

Portable devices 620 and 640 may be small, lightweight and otherwise unobtrusive devices that are well-situated for being carried by a person. Thus, for example, portable devices 620 and 640 may easily fit into a pocket, into a wallet or purse, around a wrist, on a keychain, etc. Portable devices 620 and 640 may be battery-operated and require charging from time to time (e.g., once every several days, weeks, or months). Portable device 620 may include BLE module 622 which is capable of pairing with BLE modules of other devices, for example with BLE module 614 of mobile device 610 as shown. Likewise, portable device 640 may include BLE module 642 that is capable of pairing with BLE modules of other devices, for example with BLE module 634 of mobile device 630 as shown.

Portable devices 620 and 640 may be configured to detect and record the presence of other BLE devices in their respective proximities. The range of these proximities may vary from device to device based on available power, quality of wireless signals, and other factors. But in most embodiments, the presence of other BLE devices within a few (e.g., 0 to 5) meters may be detected and recorded. Such detection may take place as part of a BLUETOOTH® protocol in which BLE devices periodically or from time to time scan wireless frequencies for the presence of other BLE devices. In response to detection of another BLE device, a unique identifier of that device, such as its medium access control (MAC) address, and the time of the detection may be recorded and stored temporarily on the detecting BLE device. The detecting BLE device may then transmit the recorded information to its paired mobile device for longer-term storage, and the BLE device may eventually delete the recorded information. For example, the BLE device may flush all recorded information that was transmitted to its paired mobile device once per day or that is older than a predetermined threshold amount of time (e.g., two weeks).

B. Initialization

Figure 7:
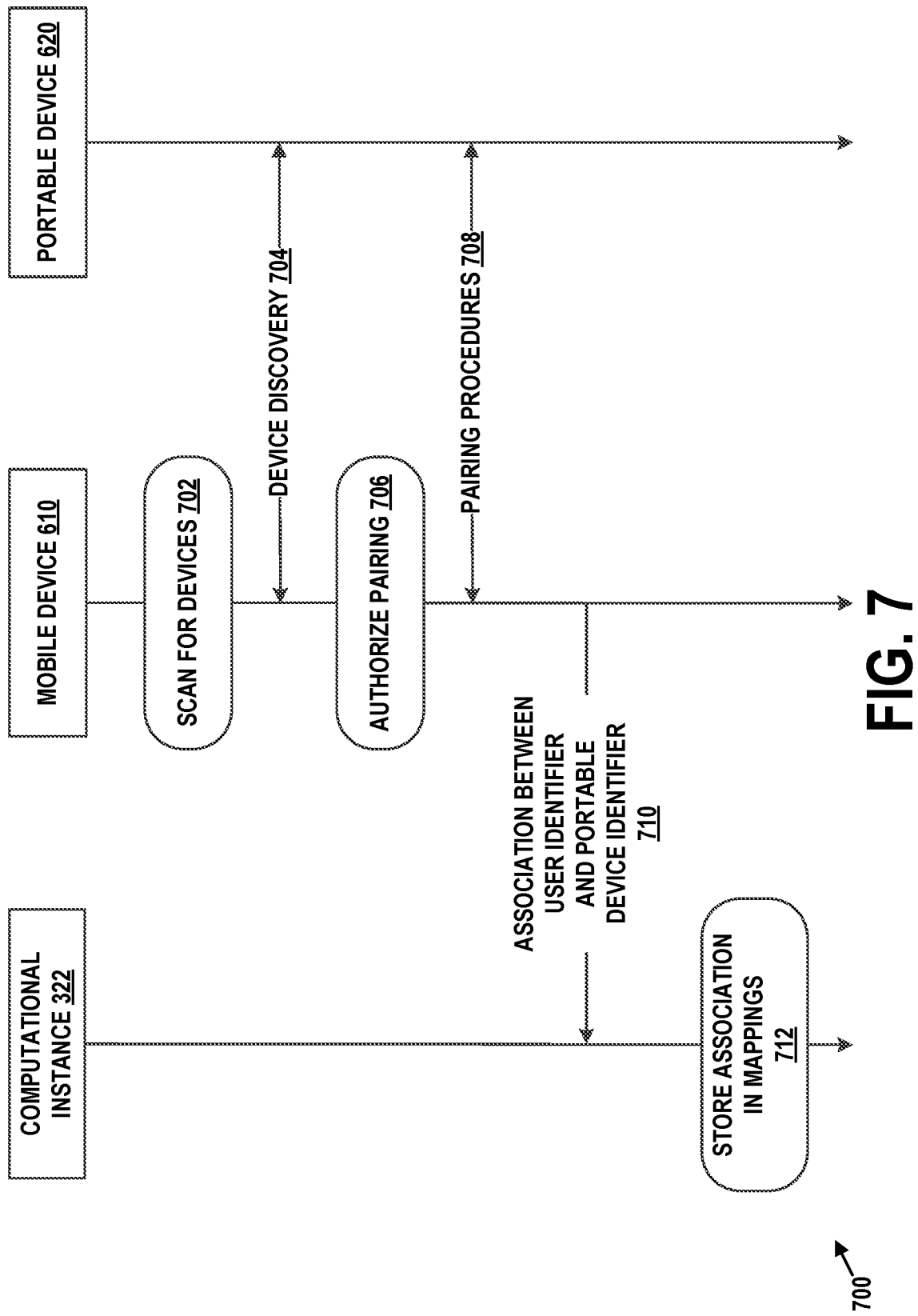
FIG. 7 is a message flow diagram for initialization, in accordance with example embodiments.

FIG. 7 depicts initialization procedure 700 for pairing mobile device 610 with portable device 620 by way of a personal area network such as a BLE network. Procedure 700 assumes that the user of mobile device 610 has been issued portable device 620 for purposes of contact tracing and that mobile device 610 and portable device 620 have not yet been paired with one another. In some embodiments, however, initialization procedure 700 can be used to re-pair previously paired devices. While BLE is used throughout these embodiments for purposes of example, other personal area network technologies, such as BLUETOOTH®, IBEACON®, ESTIMOTE®, Gimbal, ONYX BEACON®, or StickNFind may be used.

BLE is a short-range radio frequency (RF) technology that can be operated in at least the 2.4 GHz range. It can use frequency hopping to minimize interference caused by IEEE 802.11 (Wife), microwave ovens, and other BLE devices. BLE communications can be point-to-point or point-to-multipoint at speeds up to 1 Mbps. BLE signals do not require line-of-sight, can travel through most physical barriers, and have a range of approximately 10 meters.

To discover remote BLE devices, a local BLE device may enter the inquiry sub-state. There may be a number of different inquiry access codes, each of which allow a BLE device to specify the type of device it is seeking, such as a mobile device, a printer, or a WiFi access point. When in the inquiry sub-state, the local BLE device may generate a channel hopping sequence derived from its clock and the inquiry access code. The hopping sequence can, for example, include a 32-channel subset of the available 79 BLE channels. The local BLE device then broadcasts inquiry messages as it sequentially switches to each channel in the hopping sequence.

Discoverable remote BLE devices will periodically enter the inquiry scan sub-state. In this sub-state, the devices hop according to an inquiry scan hopping sequence, which is based on their respective inquiry access codes and local clocks. If a remote BLE device (a device performing the inquiry scan) receives an inquiry message, it enters the inquiry response sub-state and replies with an inquiry response message. The inquiry response includes the remote BLE device's address (e.g., a unique 48-bit MAC address) and clock.

Some or all discoverable remote BLE devices within the range of the local BLE device may respond to the device inquiry. From the remote BLE devices that have responded to the inquiry, an application operating on the local BLE device or a user thereof may select the desired responding device from a list of discovered remote BLE devices. During this process, the local BLE device and the selected remote BLE device each learns the others' respective BLE address.

After obtaining the remote device's BLE address, the local BLE device enters the paging sub-state to establish a connection with the remote BLE device. In the paging sub-state, the local BLE device generates a hopping sequence based on the remote BLE device's address and estimated current clock. The local BLE device then sends one or more page messages as it hops through the sequence of channels.

The remote BLE device (if it allows other devices to connect to it) may periodically enter the page scan sub-state. In this sub-state, a hopping sequence is generated based on its local address and clock. When the remote BLE device receives a page message, it responds to the local BLE device with a page response packet.

Upon receiving the response, the local BLE device sends a frequency hopping synchronization (FHS) packet to the remote BLE device. The FHS packet includes the local BLE device's address and clock. Once the remote BLE device receives the FHS packet, it sends an acknowledgement to the local BLE device. When the local BLE device receives the acknowledgement, it generates a new hopping sequence from its own address and its own clock. The remote BLE device then uses the local BLE device's address and clock to generate a hopping sequence identical to the local BLE device's hopping sequence. The identical hopping sequences allow the devices to hop to the same channels at the same times while remaining connected.

Once the paging process is complete, both devices move to the connection state. The local BLE device sends a poll packet to the remote BLE device verifying that the transition from the page hopping sequence to the new hopping sequence is successful. If successful, the two devices may communicate with one another. During this communication, they may continue frequency hopping in a pseudo-random pattern based on the local BLE device's address and clock for the duration of the connection.

Note that the description above may apply to devices using BLE. Other short range wireless technologies may use similar or different mechanisms for device discovery and/or communication. Furthermore, the designations "local BLE device" and "remote BLE device" are for purposes of convenience. In various embodiments, any BLE device may assume the role of a local BLE device or a remote BLE device.

Using these or similar mechanisms, mobile device 610 and portable device 620 may pair with one another so that there is a communicative relationship between the devices. The pairing process may be triggered by way of user request from the BLUETOOTH® settings of mobile device 610 or via mobile application 612.

For instance, as shown at step 702 of FIG. 7, the user of mobile device 610 may request that mobile device 610 scan for other BLE devices in the vicinity. At step 704, in response to this request, mobile device 610 may carry out such a scan, detect portable device 620, and conduct device discovery procedures with portable device 620. Mobile device 610 may then prompt the user (e.g., by way of a user interface) for authorization to pair with portable device 620.

At step 706, the user may authorize this pairing. At step 708, in response to the pairing being authorized, mobile device 610 and portable device 620 may carry out pairing procedures. During either or both of steps 704 and 708, mobile device 610 (and in particular mobile application 612) may become aware of the unique portable device identifier of portable device 620 (i.e., a MAC address). A result of the pairing may also be the generation of a shared secret or key that can be used to secure (e.g., encrypt and/or authenticate) BLE communications between mobile device 610 and portable device 620.

Once the devices are paired, the user may launch, activate, or otherwise switch to mobile application 612. From a user interface of this application, the user may indicate that the pairing with portable device 620 for purposes of contact tracing is complete. Mobile application 612 may also be configured with a unique user identifier of the user (e.g., a name, employee number, government-issued number, email address, etc.).

At step 710, mobile device 610 may transmit an association between the user identifier and the portable device identifier to computational instance 322. This association may be a tuple including the user identifier, the portable device identifier, and possibly other information, such as an identifier of mobile device 610, a timestamp of when the pairing occurred, and so on.

At step 712, computational instance 322 may store the association in mappings 602. If an association for either or both of the user identifier and the portable device identifier already exists, this mapping or mappings may be updated by the association. Thus if a user misplaces or loses his or her issued portable device, or if the portable device breaks, the enterprise can issue a new portable device to the user and mapping 602 may be updated accordingly.

Figure 8:
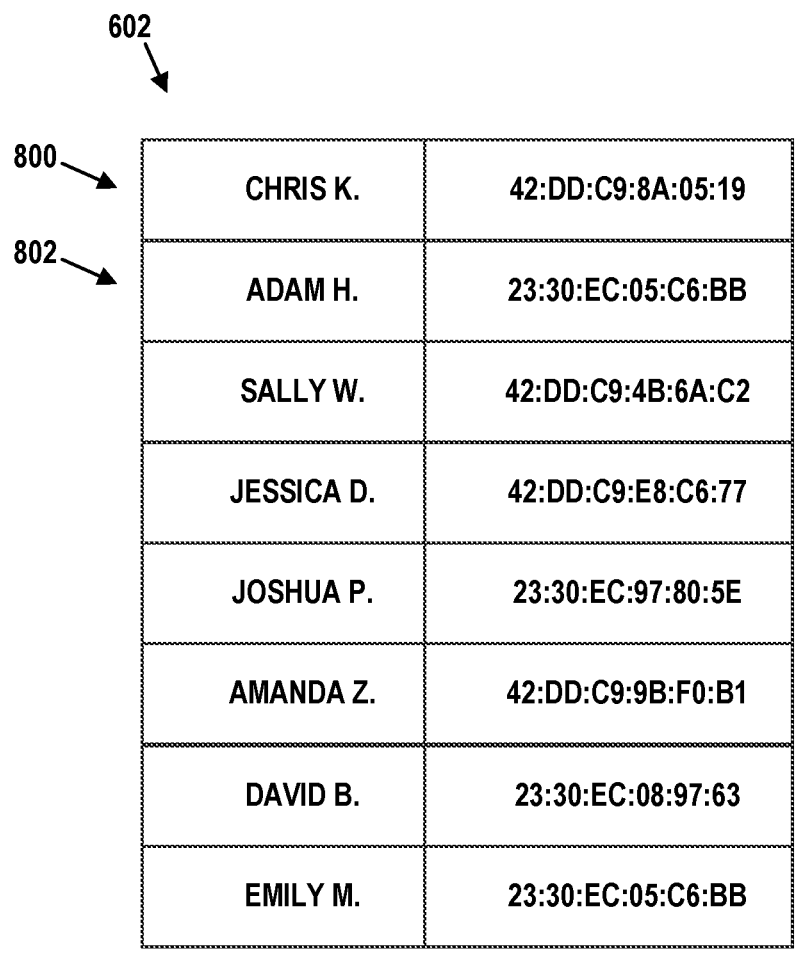
FIG. 8 depicts mappings, in accordance with example embodiments.

With numerous mobile devices following this process, mappings 602 can be populated with tens, hundreds, or thousands of associations between user identifiers and portable device identifiers. An example of mappings 602 is shown in FIG. 8. Each association in this example is a pairwise tuple between a user identifier and a portable device identifier. Here, the user identifiers are names of the users and the portable device identifiers are MAC addresses of the portable devices that were issued to the user and paired with his or her mobile device.

For example, association 800 is between user Chris K. and the portable device with a MAC address of 42:DD:C9:8A:05:19. Likewise, association 802 is between user Adam H. and the portable device with a MAC address of 23:30:EC:05:C6:BB. Mappings 602 also contains a number of similar associations. As noted above, each association may contain additional information above and beyond just user identifiers and portable device identifiers.

C. Contact Recording

During day-to-day operations of the enterprise, portable devices may come within proximity of one another. For example, such a portable device may carry out routine scans for other BLE devices within wireless range. During or after such a scan, records of contacts with BLE devices discovered in this fashion may be stored at least temporarily in the portable device. These records may contain the unique identifiers of the contacted BLE devices along with timestamps of when the contacts occurred. Periodically or from time to time, the portable device may transmit copies of the records to its paired mobile device, and the mobile device may store the records as entries of device adjacency data.

Thus, as users move about in an enterprise facility, their portable devices may record when pairs of these users are in contact. Such a contact may not require physical contact, but instead can be recorded whenever the portable devices detect that they are within wireless range of one another. In some embodiments, a contact might only be recorded when the portable devices are within range of one another and detect at least a threshold signal strength from another BLE device. As pathogens are unlikely to be transmitted between individuals who are more than 2-3 meters apart, this threshold can be tuned so that contacts between users that are more than 2-3 meters from one another are unlikely to be recorded.

Further, a portable device carried by a user may detect, from time to time, device identifiers of other BLE devices that are not being used for contact tracing (e.g., nearby phones, computers, fitness monitors, inventory trackers, etc.). The portable device might not be able to tell the difference between the device identifiers of other portable devices used for contact tracing and these more generic BLE devices that are not being used for contact tracing. Thus, the portable device may record all such contacts, and records that do not involve portable devices used for contact tracing may be removed from consideration in later processing (e.g., by computational instance 322 once a user reports an adverse condition).

Figure 9:
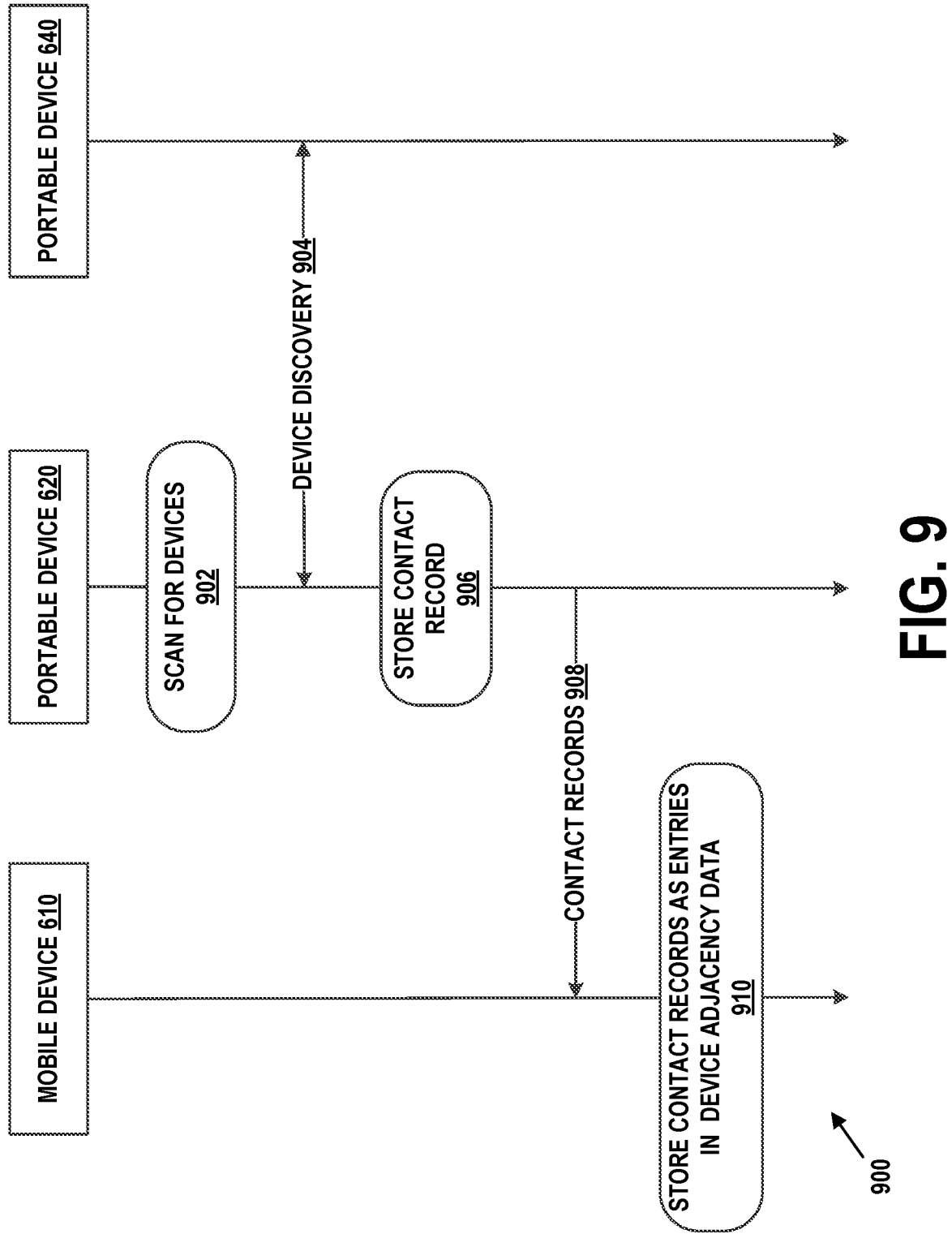
FIG. 9 is a message flow diagram for recording contact, in accordance with example embodiments.

Message flow diagram 900 of FIG. 9 depicts contact recording procedures. At step 902, portable device 620 may scan for nearby BLE devices. During this scanning process, portable device 620 may discover nearby portable device 640.

At step 904, portable device 620 and portable device 640 may engage in device discovery procedures. As part of this step, portable device 620 may become aware of a unique portable device identifier of portable device 640 (e.g., a MAC address).

At step 906, portable device 620 may store a contact record for its contact with portable device 640. This record may include the unique portable device identifier of portable device 640 as well as a timestamp of when the contact occurred.

At step 908, which may take place immediately after step 906 or some number of minutes, hours, or days after step 906, portable device 620 transmits the contact records to mobile device 610. Step 908 may be triggered by the expiration of a timer on portable device 620, memory within portable device 620 exceeding a predefined utilization threshold (e.g., 80%), or upon request from mobile device 610. For example, mobile application 612 may be configured to request new contact records from portable device 620 once per day or on demand. After step 908, portable device 620 may delete the transmitted contact records in order to save memory space and/or to be in compliance with privacy concerns.

At step 910, mobile device 610 may store the received contact records as entries in device adjacency data 616. These entries may remain in device adjacency data 616 until requested by computational instance 322 or a predefined period of time associated with an incubation period of a pathogen has passed (e.g., two weeks). In some embodiments, these contact records may be encrypted with a shared secret key that is known to computational instance 322 and portable device 620, but not mobile device 610. Thus, the user of mobile device 610 might not be able to determine the actual content of device adjacency data 616.

Figure 10:
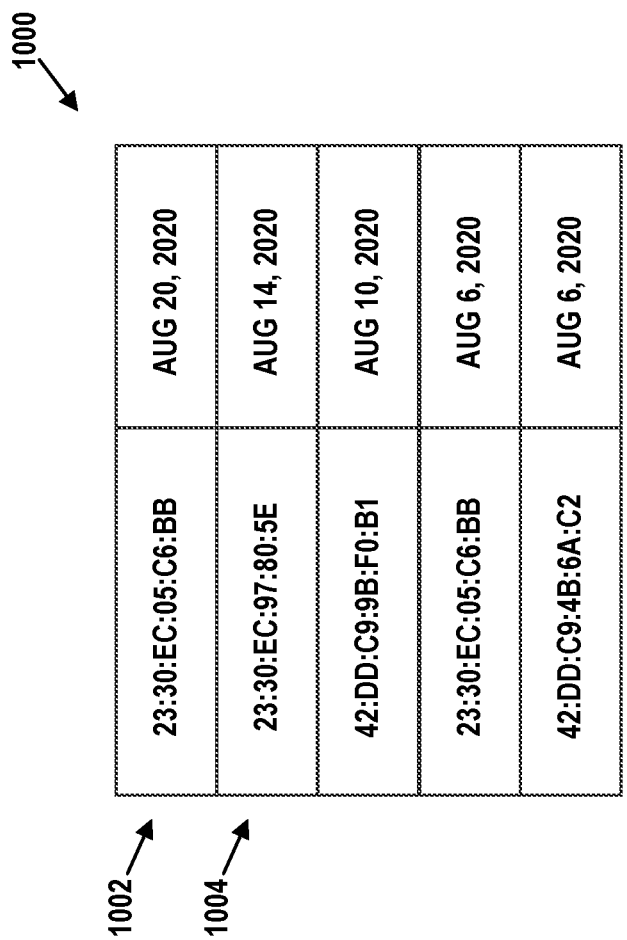
FIG. 10 depicts contact records, in accordance with example embodiments.

FIG. 10 provides example contact records 1000. The information in FIG. 10 may be stored as contact records in a portable device, or as device adjacency data entries in a mobile device.

Each of contact records 1000 may associate a portable device identifier with a timestamp. As noted, the portable device identifier specifies a portable device with which contact has been made, and the timestamp specifies the time of this contact.

For instance, record 1002 indicates that contact was made on Aug. 20, 2020 with the portable device that has portable device identifier 23:30:EC:05:C6:BB. Likewise, record 1004 indicates that contact was made on Aug. 14, 2020 with the portable device that has portable device identifier 23:30:EC:97:80:5E. In various embodiments, the timestamps may be specified with more granularity, and thus include the hour, minute, and/or second of the contacts. Further, contact records 1000 could potentially include may more records.

D. Contact Tracing and Notification

Contact tracing involves receiving an indication that a user has an adverse condition (e.g., is symptomatic, has tested positive for a pathogen, or may have been exposed to a pathogen), and then notifying other users with which the user has been in contact that they may have been exposed to the pathogen. In addition to notifying these first-order contacts, one or more second-order contacts (i.e., users with which these other users have been in contact) may be notified. In some cases, third-order contacts, fourth-order contacts and so on may also be notified. Thus, this process effectively builds a tree of contacts with the initial user that has the adverse condition at its root. This can be done in a recursive or iterative fashion.

In some cases, this tree may be pruned based on the timing of contacts and the incubation period of the pathogen. For example, contacts more than two weeks before the initial user reported the adverse condition may be omitted. Further, in situations where the initial user had a contact with user u1 on August 20 and user u1 had a contact with user u2 on August 19, the contact between users u1 and u2 may be omitted because user u1 had not been exposed to the initial user on August 19. Other pruning scenarios may exist.

As noted above, in some cases, device adjacency data may identify BLE devices that are not of the portable devices issued for purposes of contact tracing. These devices may be omitted from contact tracing and notification procedures. For instance, computational instance 322 may contain a list of all BLE devices issued for purposes of contact tracing, and may ignore device adjacency data entries involving a BLE device not on this list.

Once a user has been notified, they may be required or asked to self-quarantine for a period of time (e.g., one week or two weeks) and therefore not report to the enterprise's facilities in person. In this way, the spread of the pathogen can be mitigated.

Figure 11:
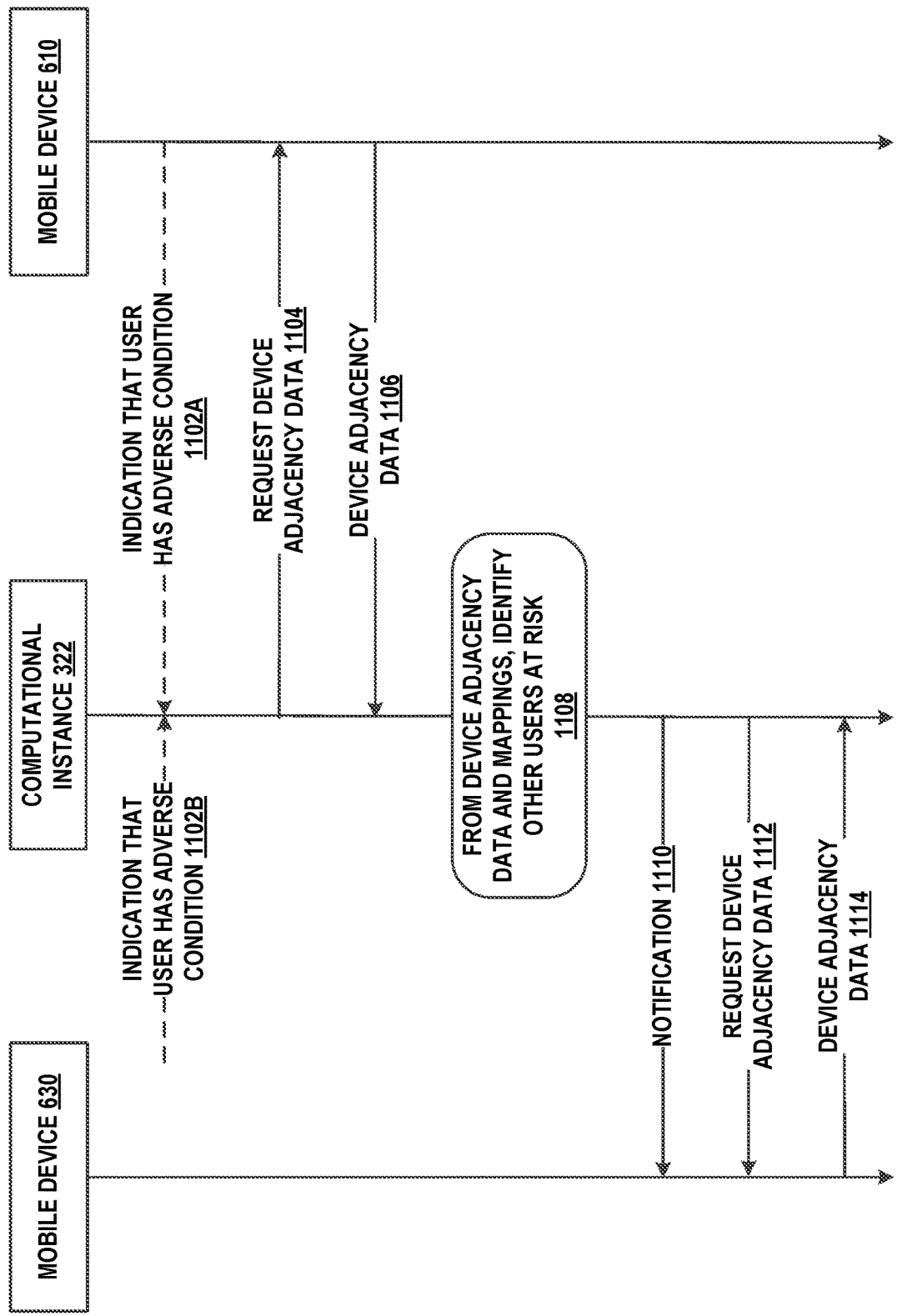
FIG. 11 is a message flow diagram, in accordance with example embodiments.

Message flow diagram 1100 of FIG. 11 depicts the first iteration of an example contact tracing and notification process. At steps 1102A or 1102B, computational instance 322 may receive an indication that a particular user has an adverse condition. In some cases, this indication may come from the particular user specifying that they have the adverse condition by way of a user interface of mobile device 610. Then, mobile device 610 may transmit the indication to computational instance 322. In other cases, the particular user may provide the indication to the enterprise by way of phone, text message, email, or some other mechanism, and enterprise personnel may manually provide the indication to computational instance 322. The indication may include the user identifier of the particular user.

In response to receiving the indication, computational instance 322 may, at steps 1104 and 1106, request and receive device adjacency data 616 from mobile device 610. This may involve computational instance 322 determining an account of the user based on the user identifier of the particular user, determining that mobile device 610 is associated with the account, and transmitting the request to mobile device 610.

At step 1108, computational instance 322 may, using device adjacency data 616 and mappings 602, identify other users at risk of being infected by the pathogen. These other users may be determined as described above. As one example, suppose that device adjacency data 616 indicates that the user associated with portable device 640 was in contact with the particular user less than one day prior to the particular user reporting the adverse condition. Then, computational instance may look up the portable device identifier of portable device 640 in mappings 602. The result of this lookup may be the user identifier of the user associated with portable device 640. From this user identifier, computational instance may also determine the account and mobile device of this user (i.e., mobile device 630).

Thus, at step 1110, computational instance 322 may transmit a notification to mobile device 630. This notification may indicate that the user of this device may have been exposed to a pathogen, as well as recommended remedial steps (e.g., self-quarantine, seeking medical testing, etc.). To preserve user privacy, the notification might not identify which contact led to this potential exposure or when that contact occurred.

In addition to this user being notified, second-order contacts may be determined by obtaining device adjacency data 636 from mobile device 630. Thus, at steps 1112 and 1114, computational instance 322 may request and receive device adjacency data 636. With device adjacency data 636 on hand, computational instance 322 can determine second-order contacts. This process is not shown in FIG. 11 because it is similar to steps 1108, 1110, 1112, and 1114. In general, steps 1110, 1112, and 1114 could be performed for many mobile devices that are identified by computational instance 322 when processing device adjacency data 616.

E. Privacy Improvements

Such a system described by architecture 600, where data is spread over multiple sources, may be advantageous in light of privacy concerns. In particular, architecture 600 may be applied to a system of devices such that the enterprise might not have simultaneous control over all aspects of user data.

For instance, mappings identifying users may be stored in an encrypted field in CMDB 500 to which the users of the mobile devices do not have access. A designated person within the enterprise may have access to mappings 602, but might not have access to the users with whom the users of each mobile device interacted unless a user reports that they are subject to an adverse condition. The users of each mobile device may have access to the device adjacency data stored on each mobile device, but might not have access to mappings 602. Alternatively, entries in the device adjacency data stored on each mobile device may be encrypted with a key not known to the users. Additionally, the device adjacency data may be updated such that the oldest entries are erased after a time period or after a threshold number of entries is exceeded.

Further, if a user does not wish to have their contacts recorded (e.g. when they are at home), the user may unpair, turn off, or disconnect their mobile device, e.g. mobile device 610, from the corresponding portable device, e.g. portable device 620. In some cases, the user may physically distance portable device 620 from mobile device 610 such that BLUETOOTH® or BLE communications between these devices can no longer occur.

Still further, if a user reports that they are subject to an adverse condition, their privacy may also be maintained through the system described by architecture 600. Since device adjacency data may contain anonymous device identifiers, users notified that they may have been in contact with a symptomatic individual may not be able to determine from their device adjacency data the specific symptomatic individual.

VI. Example Operations

Figure 12:
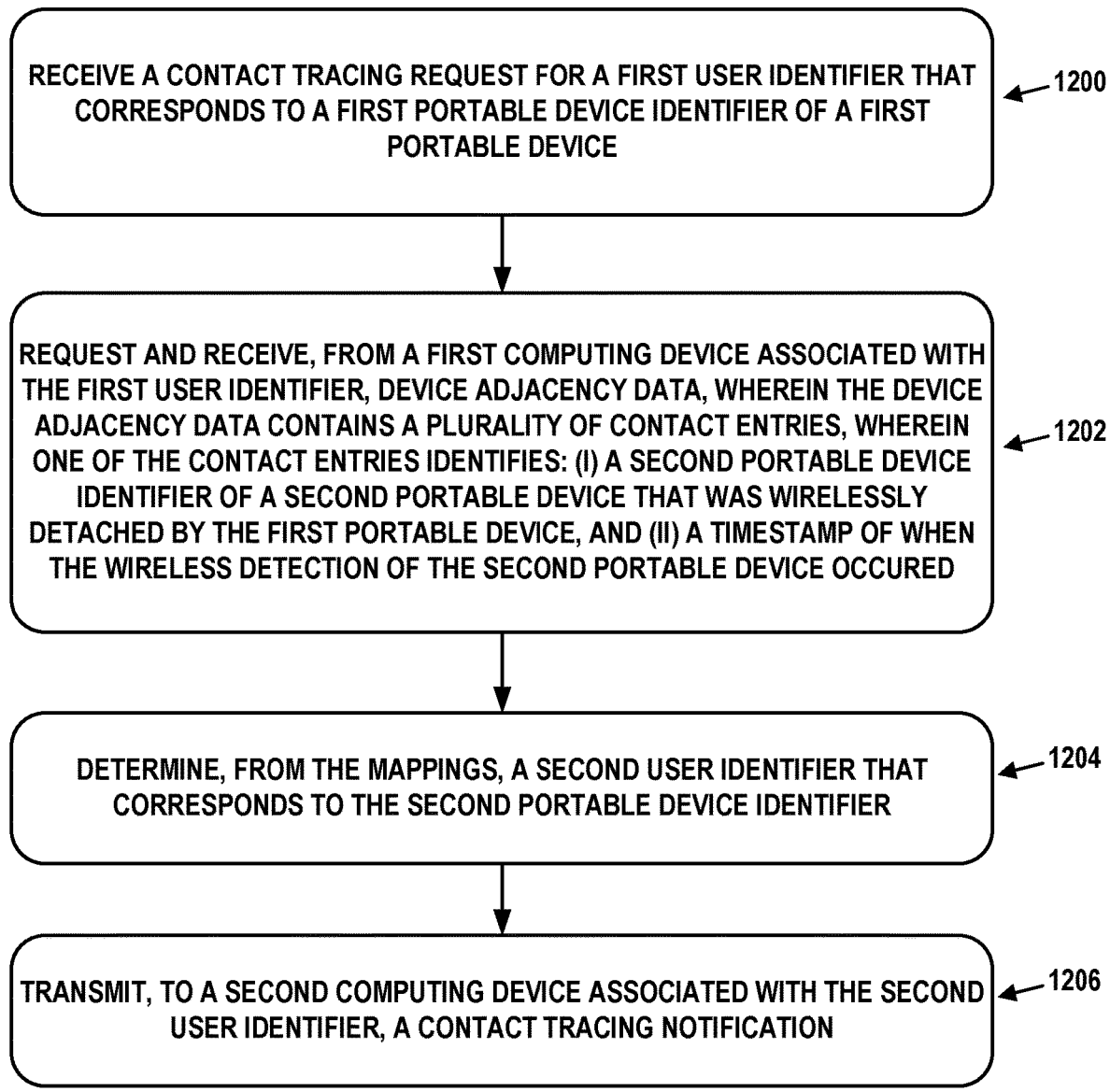
FIG. 12 is a flow chart, in accordance with example embodiments.

FIG. 12 is a flow chart illustrating an example embodiment. The process illustrated by FIG. 12 may be carried out by a computing device, such as computing device 100, and/or a cluster of computing devices, such as server cluster 200. However, the process can be carried out by other types of devices or device subsystems. For example, the process could be carried out by a computational instance of a remote network management platform or a portable computer, such as a laptop, a tablet device, or a mobile device.

The embodiments of FIG. 12 may be simplified by the removal of any one or more of the features shown therein. Further, these embodiments may be combined with features, aspects, and/or implementations of any of the previous figures or otherwise described herein.

Block 1200 may involve receiving a contact tracing request for a first user identifier that corresponds to a first portable device identifier of a first portable device, wherein persistent storage contains mappings between user identifiers and portable device identifiers respectively corresponding to the user identifiers.

Block 1202 may involve requesting and receiving, from a first computing device associated with the first user identifier, device adjacency data, wherein the device adjacency data contains a plurality of contact entries, wherein one of the contact entries identifies: (i) a second portable device identifier of a second portable device that was wirelessly detected by the first portable device, and (ii) a timestamp of when the wireless detection of the second portable device occurred.

Block 1204 may involve determining, from the mappings, a second user identifier that corresponds to the second portable device identifier.

Block 1206 may involve transmitting, to a second computing device associated with the second user identifier, a contact tracing notification.

In some embodiments, the contact tracing request was received from the first computing device.

In some embodiments, the wireless detection is based on a distance estimation meeting a distance threshold between the first portable device and the second portable device.

In some embodiments, the contact tracing request indicates that a first user associated with the first user identifier is symptomatic of a pathogen, has tested positive for the pathogen, or may have been exposed to the pathogen.

In some embodiments, the contact tracing notification indicates that a second user associated with the second user identifier has potentially been in contact with the first user.

In some embodiments, the contact tracing notification further indicates the timestamp associated with when the wireless detection of the second portable device occurred.

In some embodiments, the contact entries identifies: (i) a third portable device identifier of a third portable device that was wirelessly detected by the first portable device, and (ii) a further timestamp of when the wireless detection of the third portable device occurred. The one or more processors are further configured to determine, from the mappings, a third user identifier that corresponds to the third portable device identifier and transmit, to a third computing device associated with the third user identifier, a further contact tracing notification.

In some embodiments, the persistent storage also contains a representation of an incubation period of a pathogen. The one or more processors are further configured to determine that the timestamp is within the incubation period, wherein determining the second user identifier and transmitting the contact tracing notification is caused by the timestamp being within the incubation period.

In some embodiments, the first computing device stores a representation of an incubation period of a pathogen, and wherein the first computing device only provides contact entries that occurred within the incubation period.

In some embodiments, the one or more processors are further configured to request and receive, from the second computing device associated with the second user identifier, a second set of device adjacency data, wherein the second set of device adjacency data contains a second plurality of contact entries, wherein one of the contact entries in the second plurality of contact entries identifies: (i) a third portable device identifier of a third portable device that was wirelessly detected by the second portable device, and (ii) a further timestamp of when the wireless detection of the third portable device occurred. The one or more processors are also configured to determine, from the mappings, a third user identifier that corresponds to the third portable device identifier. The one or more processors are further configured to transmit, to a third computing device associated with the third user identifier, a further contact tracing notification.

In some embodiments, the third computing device stores a representation of an incubation period of a pathogen, and wherein the third computing device only provides contact entries that occurred within the incubation period.

In some embodiments, the wireless detection occurs through Bluetooth Low Energy communication protocol.

In some embodiments, the first portable device identifier is a first media access control (MAC) address corresponding to the first portable device and wherein the second portable device identifier is a second MAC address corresponding to the second portable device.

In some embodiments, the first computing device is a first mobile device and the second computing device is a second mobile device.

VII. Closing

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer readable medium such as a storage device including RAM, a disk drive, a solid state drive, or another storage medium.

The computer readable medium can also include non-transitory computer readable media such as computer readable media that store data for short periods of time like register memory and processor cache. The computer readable media can further include non-transitory computer readable media that store program code and/or data for longer periods of time. Thus, the computer readable media may include secondary or persistent long term storage, like ROM, optical or magnetic disks, solid state drives, or compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed is:

1. A system comprising:
    persistent storage containing mappings between user identifiers and portable device identifiers respectively corresponding to the user identifiers; and
    one or more processors configured to:
        receive a contact tracing request for a first user identifier that corresponds in the mappings to a first portable device identifier of a first portable device;
        request and receive, from a first computing device associated with the first user identifier, device adjacency data, wherein the device adjacency data contains a plurality of contact entries, wherein one of the contact entries identifies: (i) a second portable device identifier of a second portable device that was wirelessly detected by the first portable device, and (ii) a timestamp of when the wireless detection of the second portable device occurred;
        determine, from the mappings, a second user identifier that corresponds to the second portable device identifier; and
        transmit, to a second computing device associated with the second user identifier, a contact tracing notification.

2. The system of claim 1, wherein the contact tracing request was received from the first computing device.

3. The system of claim 1, wherein the wireless detection is based on a distance estimation meeting a distance threshold between the first portable device and the second portable device.

4. The system of claim 1, wherein the contact tracing request indicates that a first user associated with the first user identifier is symptomatic of a pathogen, has tested positive for the pathogen, or may have been exposed to the pathogen.

5. The system of claim 4, wherein the contact tracing notification indicates that a second user associated with the second user identifier has potentially been in contact with the first user.

6. The system of claim 5, wherein the contact tracing notification further indicates the timestamp associated with when the wireless detection of the second portable device occurred.

7. The system of claim 1, wherein another of the contact entries identifies: (i) a third portable device identifier of a third portable device that was wirelessly detected by the first portable device, and (ii) a further timestamp of when the wireless detection of the third portable device occurred, and wherein the one or more processors are further configured to:
    determine, from the mappings, a third user identifier that corresponds to the third portable device identifier; and
    transmit, to a third computing device associated with the third user identifier, a further contact tracing notification.

8. The system of claim 1, wherein the persistent storage also contains a representation of an incubation period of a pathogen, and wherein the one or more processors are further configured to:
    determine that the timestamp is within the incubation period, wherein determining the second user identifier and transmitting the contact tracing notification is caused by the timestamp being within the incubation period.

9. The system of claim 1, wherein the first computing device stores a representation of an incubation period of a pathogen, and wherein the first computing device only provides contact entries that occurred within the incubation period.

10. The system of claim 1, wherein the one or more processors are further configured to:
    request and receive, from the second computing device associated with the second user identifier, a second set of device adjacency data, wherein the second set of device adjacency data contains a second plurality of contact entries, wherein one of the contact entries in the second plurality of contact entries identifies: (i) a third portable device identifier of a third portable device that was wirelessly detected by the second portable device, and (ii) a further timestamp of when the wireless detection of the third portable device occurred;

determine, from the mappings, a third user identifier that corresponds to the third portable device identifier; and transmit, to a third computing device associated with the third user identifier, a further contact tracing notification.

11. The system of claim 10, wherein the third computing device stores a representation of an incubation period of a pathogen, and wherein the third computing device only provides contact entries that occurred within the incubation period.

12. The system of claim 1, wherein the wireless detection occurs through Bluetooth Low Energy communication protocol.

13. The system of claim 1, wherein the first portable device identifier is a first media access control (MAC) address corresponding to the first portable device and wherein the second portable device identifier is a second MAC address corresponding to the second portable device.

14. The system of claim 1, wherein the first computing device is a first mobile device and the second computing device is a second mobile device.

15. A computer-implemented method comprising:

receiving a contact tracing request for a first user identifier that corresponds to a first portable device identifier of a first portable device, wherein persistent storage contains mappings between user identifiers and portable device identifiers respectively corresponding to the user identifiers;

requesting and receiving, from a first computing device associated with the first user identifier, device adjacency data, wherein the device adjacency data contains a plurality of contact entries, wherein one of the contact entries identifies: (i) a second portable device identifier of a second portable device that was wirelessly detected by the first portable device, and (ii) a timestamp of when the wireless detection of the second portable device occurred;

determining, from the mappings, a second user identifier that corresponds to the second portable device identifier; and transmitting, to a second computing device associated with the second user identifier, a contact tracing notification.

16. The method of claim 15, wherein the contact tracing request was received from the first computing device.

17. The method of claim 15, wherein the wireless detection is based on a distance estimation meeting a distance threshold between the first portable device and the second portable device.

18. The method of claim 15, wherein the contact tracing request indicates that a first user associated with the first user identifier is symptomatic of a pathogen, has tested positive for the pathogen, or may have been exposed to the pathogen.

19. The method of claim 18, wherein the contact tracing notification indicates that a second user associated with the second user identifier has potentially been in contact with the first user.

20. An article of manufacture including a non-transitory computer-readable medium, having stored thereon program instructions that, upon execution by a computing system, cause the computing system to perform operations comprising:

receiving a contact tracing request for a first user identifier that corresponds to a first portable device identifier of a first portable device, wherein persistent storage contains mappings between user identifiers and portable device identifiers respectively corresponding to the user identifiers;

requesting and receiving, from a first computing device associated with the first user identifier, device adjacency data, wherein the device adjacency data contains a plurality of contact entries, wherein one of the contact entries identifies: (i) a second portable device identifier of a second portable device that was wirelessly detected by the first portable device, and (ii) a timestamp of when the wireless detection of the second portable device occurred;

determining, from the mappings, a second user identifier that corresponds to the second portable device identifier; and transmitting, to a second computing device associated with the second user identifier, a contact tracing notification.

* * * * *